(12) United States Patent
Birch

(10) Patent No.: US 11,899,016 B2
(45) Date of Patent: Feb. 13, 2024

(54) METHODS OF IDENTIFYING IMMUNE CELLS IN PD-L1 POSITIVE TUMOR TISSUE

(71) Applicant: Ventana Medical Systems, Inc., Tucson, AZ (US)

(72) Inventor: Chandler Morgan Birch, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 721 days.

(21) Appl. No.: 15/985,638

(22) Filed: May 21, 2018

(65) Prior Publication Data

US 2018/0372747 A1 Dec. 27, 2018

Related U.S. Application Data

(63) Continuation of application No. PCT/EP2016/078237, filed on Nov. 21, 2016.

(60) Provisional application No. 62/258,493, filed on Nov. 22, 2015.

(51) Int. Cl.

| | | |
|---|---|---|
| G01N 33/574 | (2006.01) | |
| C07K 16/28 | (2006.01) | |
| G01N 33/50 | (2006.01) | |
| G01N 33/569 | (2006.01) | |
| C07K 16/32 | (2006.01) | |
| G01N 33/53 | (2006.01) | |
| G01N 1/31 | (2006.01) | |
| G01N 21/64 | (2006.01) | |
| G01N 33/58 | (2006.01) | |
| G01N 1/30 | (2006.01) | |
| G01N 35/00 | (2006.01) | |

(52) U.S. Cl.
CPC ......... *G01N 33/574* (2013.01); *C07K 16/289* (2013.01); *C07K 16/2812* (2013.01); *C07K 16/2815* (2013.01); *C07K 16/2818* (2013.01); *C07K 16/2827* (2013.01); *C07K 16/2863* (2013.01); *C07K 16/2896* (2013.01); *C07K 16/32* (2013.01); *G01N 1/312* (2013.01); *G01N 21/6428* (2013.01); *G01N 33/5091* (2013.01); *G01N 33/53* (2013.01); *G01N 33/56966* (2013.01); *G01N 33/582* (2013.01); *G01N 1/30* (2013.01); *G01N 2035/00138* (2013.01); *G01N 2333/70517* (2013.01); *G01N 2333/70532* (2013.01); *G01N 2333/70578* (2013.01); *G01N 2333/70589* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 6,195,451 | B1 * | 2/2001 | Kerschmann | G06T 5/50 |
| | | | | 382/133 |
| 2005/0009118 | A1 * | 1/2005 | Zhang | G01N 33/5011 |
| | | | | 435/7.23 |
| 2013/0260379 | A1 * | 10/2013 | Alexander | G01N 33/53 |
| | | | | 435/6.11 |

FOREIGN PATENT DOCUMENTS

| | | | |
|---|---|---|---|
| JP | 2004514886 A | 5/2004 | |
| JP | 2013531801 A | 8/2013 | |
| JP | 2015518826 A | 7/2015 | |
| WO | WO-0024760 A1 * | 5/2000 | ........... C12Q 1/6806 |
| WO | 0242737 A2 | 5/2002 | |
| WO | 2012003476 A2 | 1/2012 | |
| WO | 2013173223 A1 | 11/2013 | |
| WO | 2014194293 A1 | 12/2014 | |
| WO | 2015013388 A2 | 1/2015 | |
| WO | 2015088930 A1 | 6/2015 | |
| WO | 2015124703 A1 | 8/2015 | |

OTHER PUBLICATIONS

Hamanishi et al., Programmed cell death 1 ligand 1 and tumor-infiltrating CD8+ T lymphocytes are prognostic factors of human ovarian cancer, PNAS, (2007), p. 3360-3365. (Year: 2007).*
Lower, Antibody for Immunotherapy, Cancer, 2014 (1 page). (Year: 2014).*
Amersham Pharmacia Biotech (technical manual), Fluorescence Imaging, Principles and Methods, 2000 (144 pages) < https://www.bu.edu/picf/files/2010/10/Fluor-ImagingPrinciples.pdf> (Year: 2000).*
Vet et al., Multiplex detection of four pathogenic retroviruses using molecular beacons, 96, (1999), p. 6394-6399 (Year: 1999).*
Anonymous, Dual IHC on Discovery Ultra Research Instrument, Ventana Research Protocols, Jan. 1, 2014, URL: http://www.ventana.com/researchprotocols, XP055337858.
Anonymous, Dual IHC on Discovery Ultra Research Instrument, Ventana Research Protocols, Jan. 1, 2014, URL: http://www.ventana.com/researchprotocols, XP055337860.
Chen, B.J. et al., PD-L1 Expression Is Characteristic of a Subset of Aggressive B-cell Lymphomas and Virus-Associated Malignancies, Clinical Cancer Research, (2013), pp. 3462-3473, vol. 19 No. 13.
Choueiri et al., 2014, "Correlation of PD-L1 Tumor Expression and Treatment Outcomes in Patients with Renal Cell Carcinoma Receiving Sunitinib or Pazopanib: Results from COMPARZ, a Randomized Controlled Trial", Clinical Cancer Research, 21(5):1071-1077.

(Continued)

*Primary Examiner* — Ellen J Marcsisin
(74) *Attorney, Agent, or Firm* — Clark & Elbing LLP; Thomas J. Takara

(57) ABSTRACT

The present disclosure is directed to multiplex assays, kits and methods, including automated methods, for identifying PD-L1 positive immune cells, PD-L1 positive tumor cells, and PD-L1 negative immune cells within a tissue sample using two dyes selected from diaminobenzidine (DAB), 4-(dimethylamino) azobenzene-4'-sulfonamide (DABSYL), tetramethylrhodamine (DISCOVERY Purple), N,N'-biscarboxypentyl-5,5'-disulfonato-indo-dicarbocyanine (Cy5), and Rhodamine 110 (Rhodamine).

13 Claims, 11 Drawing Sheets
(9 of 11 Drawing Sheet(s) Filed in Color)

Specification includes a Sequence Listing.

(56) References Cited

OTHER PUBLICATIONS

Ghebeh et al., 2006, "The B7-H1 (PD-L1) T Lymphocyte-Inhibitory Molecule Is Expressed in Breast Cancer Patients with Infiltrating Ductal Carcinoma: Correlation with Important High-Risk Prognostic Factors", Neoplasia, 8 (3):190-198.
Ghebeh et al., 2008, "FOXP3+ Tregs and B7-H1+/PD-1+ T lymphocytes co-infiltrate the tumor tissues of high-risk breast cancer patients: Implication for immunotherapy", BMC Cancer, 8:57.
International Search Report and Written Opinion dated Mar. 31, 2017 in connection with PCT/EP2016/078237 filed Nov. 21, 2016, pp. 1-25.
Mu et al, 2011, "High expression of PD-L1 in lung cancer may contribute to poor prognosis and tumor cells immune escape through suppressing tumor infiltrating dendritic cells maturation", Medical Oncology, 28:682-688.
Shen et al, "Impaired ICOSL in human myeloid dendritic cells promotes Th2 responses in patients with allergic rhinitis and asthma", Clinical & Experimental Allergy, 44(6):831-841.
Tumeh et al, 2014, "PD-1 blockade induces responses by inhibiting adaptive immune resistance", Nature, 515(7528):568-571.
Yunmei et al, 2014, "VSIG4 expression on macrophages facilitates lung cancer development", Laboratory Investigation, 94:709-710.
=Eng et al, Multispectral imaging of formalin-fixed tissue predicts ability to generate tumorinfiltrating lymphocytes from melanoma, Journal of ImmunoTherapy of Cancer, 2015, pp. 1-11, 3: 47.

\* cited by examiner

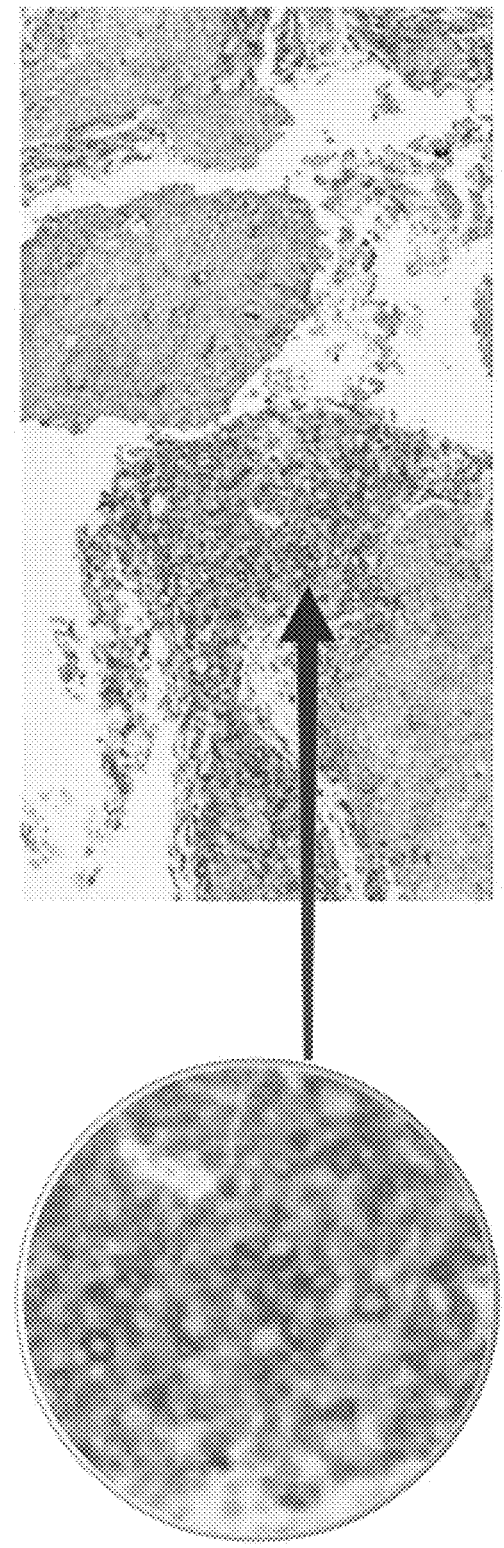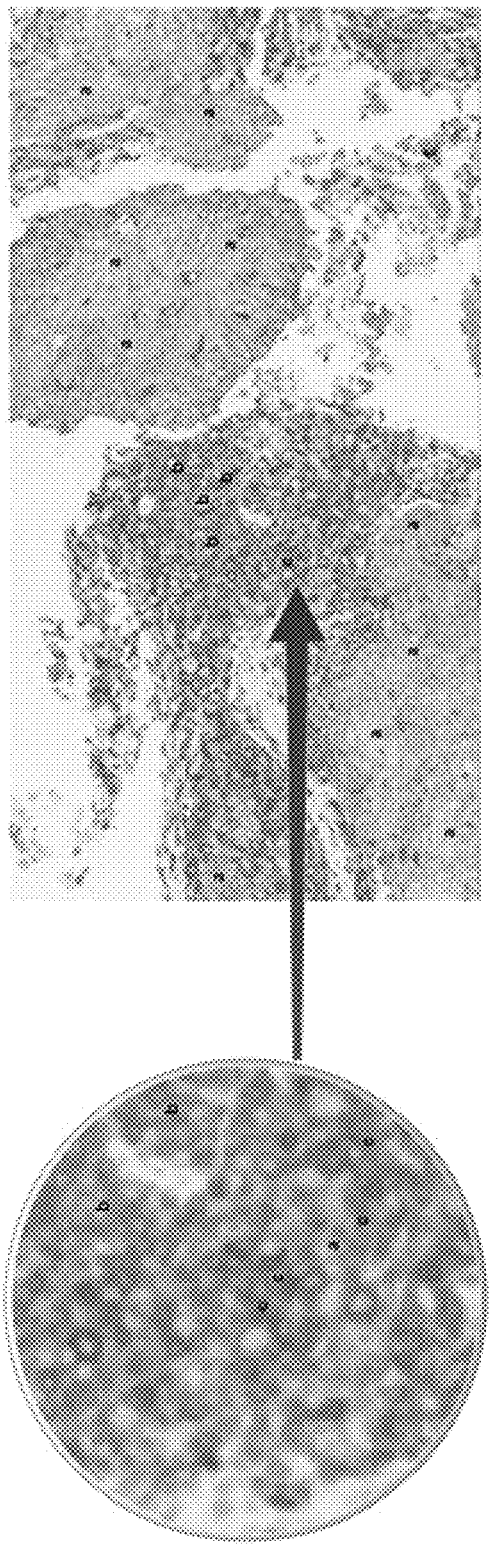
FIG. 3B
FIG. 3C

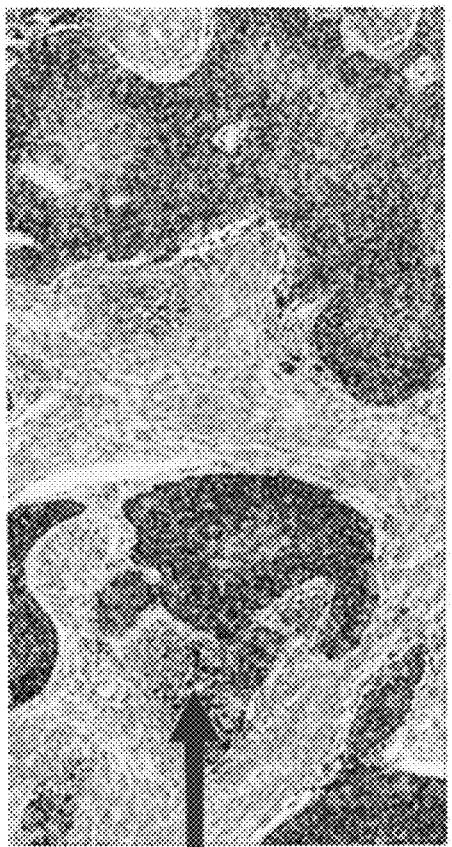
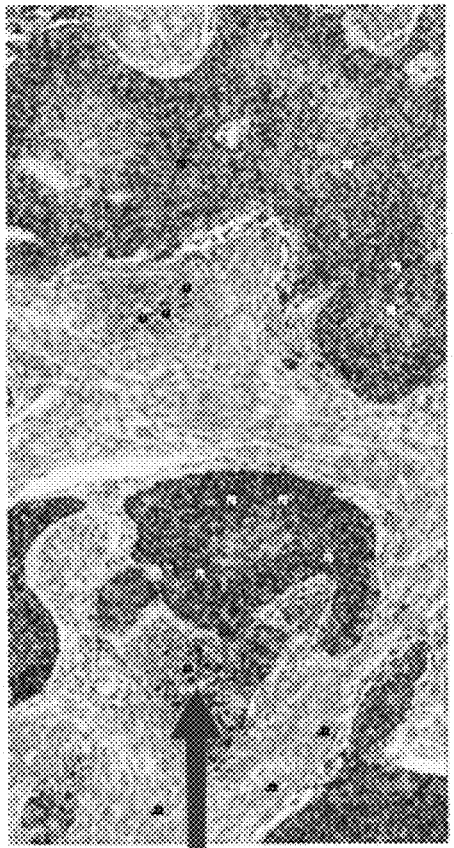
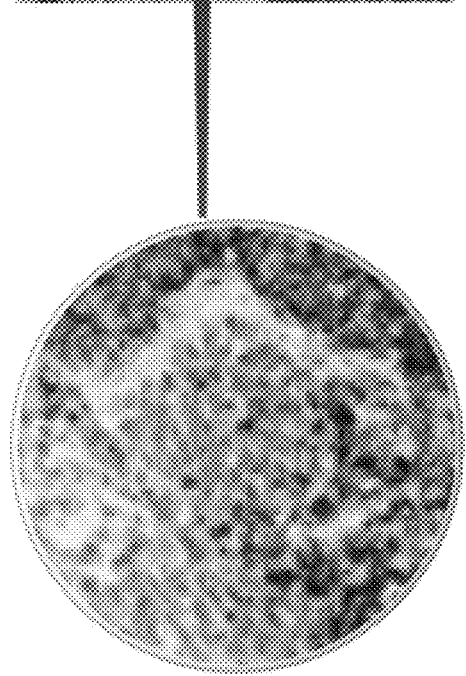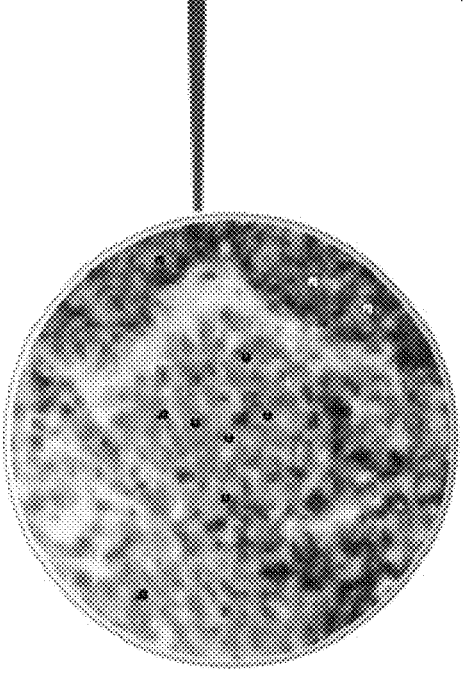
FIG. 4B
FIG. 4C

SEQUENCE LISTING

```
<160> NUMBER OF SEQ ID NOS: 5

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
```

```
                    115                 120                 125
Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 115
<212> TYPE: PRT
<213> ORGANISM: Artificial Sequence
<220> FEATURE:
<223> OTHER INFORMATION: Rabbit heavy chain sequence

<400> SEQUENCE: 2

Gln Ser Leu Glu Glu Ser Gly Gly Arg Leu Val Lys Pro Asp Glu Thr
1               5                   10                  15

Leu Thr Ile Thr Cys Thr Val Ser Gly Ile Asp Leu Ser Ser Asn Gly
            20                  25                  30

Leu Thr Trp Val Arg Gln Ala Pro Gly Glu Gly Leu Glu Trp Ile Gly
        35                  40                  45

Thr Ile Asn Lys Asp Ala Ser Ala Tyr Tyr Ala Ser Trp Ala Lys Gly
    50                  55                  60

Arg Leu Thr Ile Ser Lys Pro Ser Ser Thr Lys Val Asp Leu Lys Ile
65                  70                  75                  80

Thr Ser Pro Thr Thr Glu Asp Thr Ala Thr Tyr Phe Cys Gly Arg Ile
                85                  90                  95

Ala Phe Lys Thr Gly Thr Ser Ile Trp Gly Pro Gly Thr Leu Val Thr
            100                 105                 110

Val Ser Ser
        115

<210> SEQ ID NO 3
<211> LENGTH: 112
<212> TYPE: PRT
<213> ORGANISM: Artificial Sequence
<220> FEATURE:
<223> OTHER INFORMATION: Rabbit light chain sequence

<400> SEQUENCE: 3
```

-continued

```
Ala Ile Val Met Thr Gln Thr Pro Ser Pro Val Ser Ala Ala Val Gly
1               5                   10                  15

Gly Thr Val Thr Ile Asn Cys Gln Ala Ser Glu Ser Val Tyr Ser Asn
            20                  25                  30

Asn Tyr Leu Ser Trp Phe Gln Gln Lys Pro Gly Gln Pro Pro Lys Leu
        35                  40                  45

Leu Ile Tyr Leu Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ile Gly Gly Lys Ser Ser
                85                  90                  95

Ser Thr Asp Gly Asn Ala Phe Gly Gly Gly Thr Glu Val Val Val Arg
            100                 105                 110
```

<210> SEQ ID NO 4
<211> LENGTH: 114
<212> TYPE: PRT
<213> ORGANISM: Artificial Sequence
<220> FEATURE:
<223> OTHER INFORMATION: Rabbit heavy chain

<400> SEQUENCE: 4

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn His Ala
            20                  25                  30

Ile Ser Trp Val Arg Gln Ala Pro Gly Lys Gly Leu Glu Trp Ile Gly
        35                  40                  45

Thr Ile Asn Ser Asp Thr His Thr Tyr Tyr Ala Thr Trp Pro Lys Gly
    50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Arg
                85                  90                  95

Ile Phe Ser Ser Ser Asn Ile Trp Gly Pro Gly Thr Leu Val Thr Val
            100                 105                 110

Ser Ser
```

<210> SEQ ID NO 5
<211> LENGTH: 112
<212> TYPE: PRT
<213> ORGANISM: Artificial Sequence
<220> FEATURE:
<223> OTHER INFORMATION: Rabbit light chain

<400> SEQUENCE: 5

```
Ala Ile Val Met Thr Gln Thr Ser Ser Pro Val Ser Ala Val Val Gly
1               5                   10                  15

Gly Thr Val Ala Ile Asn Cys Gln Ala Ser Gln Ser Ile Tyr Asn Asn
            20                  25                  30

Asn Trp Leu Ser Trp Phe Gln Gln Lys Pro Gly Gln Pro Pro Lys Leu
        35                  40                  45

Leu Ile Tyr Leu Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80
```

```
Val Cys Asp Asp Ala Ala Thr Tyr Tyr Cys Ile Gly Gly Glu Ser Ser
                85                  90                  95

Asn Asn Asp Gly Ile Ala Phe Gly Gly Gly Thr Glu Val Val Val Lys
                100                 105                 110
```

METHODS OF IDENTIFYING IMMUNE CELLS IN PD-L1 POSITIVE TUMOR TISSUE

CROSS-REFERENCE TO RELATED APPLICATIONS

This patent application is a continuation of International Patent Application No. PCT/EP2016/078237 filed Nov. 21, 2016, which claims priority to and the benefit of U.S. Provisional Patent Application No. 62/258,493, filed Nov. 22, 2015. Each of the above patent applications is incorporated herein by reference as if set forth in its entirety.

SEQUENCE LISTING INCORPORATION BY REFERENCE

This application hereby incorporate-by-reference a sequence listing submitted herewith in a computer-readable format, having a file name of 33312US1_ST25, created on May 21, 2018, which is 7,201 bytes in size.

BACKGROUND

PD-1 is an immune-inhibitory receptor belonging to the CD28/CTLA4 receptor family that is expressed on activated T cells, B cells and monocytes. PD-1 is also expressed on T regulatory cells where it interacts with dendritic cells and MK T cells, and has been shown to be associated with anergy and tumor immune escape. The role of PD-1 as a negative regulator of T cell activity is mediated through its interaction with its ligands PD-L1 and PD-L2 that are expressed on immune cells and tumor cells.

PD-L1 and PD-L2 are expressed on many human tumors including melanoma, glioblastoma, non-small cell lung cancer and urothelial, ovarian, breast, cervical, colon, pancreatic and gastric carcinoma. PD-L1 has been implicated in tumor immune escape from the host immune system and in mediating tumor anti-apoptotic activity. Moreover, PD-1 ligand 1 and 2 (PD-Ls) expressed on antigen-presenting cells have been shown to indirectly induce T cell anergy or exhaustion via PD-1 on T cells, whereas PD-L1 expressed on peripheral tissues directly suppresses self-reactive lymphocytes. It is believed that PD-Ls expressed on tumors regulate the generation of adaptive regulatory T cells resulting in tumor-induced immune suppression, including the suppression of the effector function of CD8+ T cells. It is believed that higher expression levels of PD-L1 on tumors have been shown to correlate with poor prognosis in several malignant tumors including melanoma, esophagus, kidney, lung, and brain, pancreatic, ovarian and head and neck.

PD-L1 expression is measured most commonly by immunohistochemistry (IHC). Tumoral PD-L1 expression status is believed to be prognostic in multiple tumor types, including melanoma, renal cell carcinoma, and non-small-cell lung cancer. The use of PD-L1 immunohistochemistry as a predictive biomarker is confounded by multiple unresolved issues including variable detection antibodies, differing IHC cutoffs, tissue preparation, processing variability, primary versus metastatic biopsies, oncogenic versus induced PD-L1 expression, and staining of tumor versus immune cells.

WO2014/194293 ("the '293 Publication"), discloses methods for selecting patients who would be amenable for PD-L1 and B7-H4 pathway targeted therapies. The '293 Publication discloses co-staining a tissue sample with a dual CD68/B70-H1 stain, such that CD68+/B7-H1+ macrophages may be detected. The '293 Publication also discloses staining individual tissue samples with one of B7-H1, PD-1, or CD8, does not disclose staining a single tissue sample in a multiplex assay. Nor does the '293 Publication disclose contacting a tissue sample with a first detection reagent specific to PD-L1 and at least a second detection reagent specific to an immune cell marker.

WO2015/088930 ("the '930 Publication") discloses a multiplex IHC assay comprising contacting a tissue section with an antibody specific for PD-1 (anti-PD-1 Ab) and an antibody specific for the desired PD-Ligand (anti-PD Ligand Ab). The '930 Publication also discloses that cells that express PD-1 may be detected by IHC staining for expression of a molecule that extensively co-localizes with PD-1 and similarly, cells that express the PD-Ligand of interest may be detected by IHC staining for expression of a molecule that extensively co-localizes with the PD-Ligand. In such embodiments, an antibody that specifically binds to the co-localizing molecule is used as the primary antibody instead of the anti-PD-1 or anti-PD-Ligand antibody. The '930 Publication does not disclose contacting a tissue sample with a first detection reagent specific to PD-L1 and at least a second detection reagent specific to an immune cell marker.

Fent et al. "Multispectral imaging of formalin-fixed tissue predicts ability to generate tumor infiltrating lymphocytes from melanoma" J. ImmunoTherapy of Cancer, (2015)3:47 ("Feng") describes a 7-color quantitative multispectral IHC assay to analyze the immune environment of tumors from patients with melanoma. In particular, the assay disclosed is a quantitative multispectral fluorescent immunohistochemistry panel including CD3, CD8, FoxP3, CD163, PD-L1. The study was directed to studying potential suppressive mechanisms in the tumor microenvironment that may prevent the generation of autologous tumor-reactive tumor infiltrating lymphocytes. Feng does not disclose contacting a tissue sample with a first detection reagent specific to PD-L1 and at least a second detection reagent specific to an immune cell marker for the purpose of identifying those immune cells that co-express PD-L1 and the at least one other immune cell marker for the purpose of predicting a response to PD-L1 targeted therapy. Nor does Feng disclose any multiplex assay using detection reagents. Moreover, Feng does not disclose an assay that utilizes an antibody specific to CD45.

BRIEF SUMMARY OF THE INVENTION

In one aspect of the present invention is a system or kit which facilitates the identification and/or differentiation of PD-L1 positive tumor cells, PD-L1 positive immune cells, PD-L1 negative tumor cells, and/or PD-L1 negative immune cells in a tissue sample. In some embodiments, the kits comprise a first primary antibody specific for PD-L1; a second primary antibody specific for at least one immune cell marker; first detection reagents for detecting the first primary antibody; and second detection reagents for detecting the second primary antibody. In some embodiments, the at least one immune cell marker is selected from the group consisting of CD8, CD4, CD3, CD25, CD163 and CD45LCA. In some embodiments, the immune cell marker is CD45LC. In some embodiments, the first primary antibody is an anti-PD-L1 antibody (SP142) or anti-PD-L1 antibody (SP263). In some embodiments, the second primary antibody is an anti-CD45LCA antibody (RP2/18).

In some embodiments, each of the first and second detection reagents comprise (i) an enzyme; (2) reagents for depositing the enzyme in proximity to the primary antibody when the primary antibody is bound to a tissue sample, and (iii) an enzyme substrate reactive with the enzyme to deposit a dye in proximity to enzyme deposited on the sample, wherein the first and second detection reagents comprise substrates that deposit different dyes. In some embodiments, the different dyes are selected from the group consisting of diaminobenzidine (DAB), 4-(dimethylamino) azobenzene-4'-sulfonamide (DABSYL), tetramethylrhodamine (DISCOVERY Purple), N,N'-biscarboxypentyl-5,5'-disulfonato-indo-dicarbocyanine (Cy5), and Rhodamine 110 (Rhodamine). In some embodiments, a first substrate deposits one of DISCOVERY Purple or DAB, and a second substrate deposits the other of DISCOVERY Purple or DAB. In some embodiments, a first substrate deposits one of DISCOVERY Purple or DABSYL, and a second substrate deposits the other of DISCOVERY Purple or DABSYL.

In some embodiments, the kit further comprises at least one other detection probe specific for a tumor marker other than PD-L1 and detection reagents for detecting the at least one other detection probe. In some embodiments, the kit further comprises at least one other detection probe specific for EGFR, HER2, HPV, ALK, BRAF, OX-40, PD-1, IDO-1, FoxP3, CD163, and CTLA-4. In some embodiments, the kit further comprises two primary antibodies specific for at least two immune cell markers. In some embodiments, the kit further comprises components to inactivate an enzyme.

In another aspect of the present disclosure is a method of co-staining immune cells in a tissue sample comprising contacting the tissue sample with a first detection probe specific to PD-L1; contacting the tissue sample with a second detection probe specific to at least one immune cell marker; and contacting the tissue sample with first and second detection reagents, wherein the first and second detection reagents comprise substrates that effect deposition of different dyes. In some embodiments, the second detection probe is specific to CD45LCA.

In another aspect of the present disclosure is a method of identifying PD-L1 positive tumor cells, PD-L1 negative tumor cells, PD-L1 positive immune cells, and PD-L1 negative immune cells comprising contacting the tissue sample with a first detection probe specific to PD-L1; contacting the tissue sample with a second detection probe specific to at least one immune cell marker; and contacting the tissue sample with first and second detection reagents, wherein the first and second detection reagents comprise different substrates that effect deposition of different dyes. In some embodiments, the first and second detection reagents are detection reagents. In some embodiments, the second detection probe is specific to CD45LCA.

In another aspect of the present disclosure is a method of differentiating PD-L1 positive tumor cells from PD-L1 positive immune cells comprising contacting the tissue sample with a first detection probe specific to PD-L1; contacting the tissue sample with a second detection probe specific to at least one immune cell marker; and contacting the tissue sample with first and second detection reagents, wherein the first and second detection reagents comprise different substrates that effect deposition of different dyes. In some embodiments, the first and second detection reagents are detection reagents. In some embodiments, the second detection probe is specific to CD45LCA.

In another aspect of the present disclosure is a method of identifying tumor infiltrating PD-L1 positive immune cells in PD-L1 positive tumors comprising contacting a tissue sample with a first primary antibody specific to PD-L1; contacting the tissue sample with a second primary antibody specific for at least one immune cell marker; and contacting the tissue sample with first and second detection reagents, wherein the first and second detection reagents comprise different substrates that effect deposition of different dyes. In some embodiments, the tumor infiltrating PD-L1 positive immune cells co-express PD-L1 and the at least one immune cell marker. In some embodiments, the first primary antibody is anti-PD-L1 antibody SP142. In some embodiments, the immune cell marker is selected from the group consisting of CD8, CD4, CD3, CD25, CD 163 and CD45LCA. In some embodiments, the immune cell marker is CD45LCA. In some embodiments, the second antibody is anti-CD45LCA antibody RP2/18.

In some embodiments, each of the first and second detection reagents comprise (i) an enzyme, (ii) reagents for depositing the enzyme in proximity to the primary antibody when the primary antibody is bound to a tissue sample, and (iii) a substrate reactive with the enzyme to deposit a dye on the sample, wherein the first and second detection reagents comprise different substrates. In some embodiments, the different substrates are selected to deposit a dye selected from the group consisting of DAB, DABSYL, DISCOVERY Purple, Cy5, and Rhodamine. In some embodiments, a first substrate deposits one of DISCOVERY Purple or DAB, and a second substrate deposits the other of DISCOVERY Purple or DAB. In some embodiments, a first substrate deposits one of DISCOVERY Purple or DABSYL, and a second substrate deposits the other of DISCOVERY Purple or DABSYL. In some embodiments, the method further comprises contacting the tissue sample with at least one other detection probe specific for a tumor marker other than PD-L1. In some embodiments, the method further comprises contacting the tissue sample with at least one other detection probe specific for one of EGFR, HER2, HPV, ALK, BRAF, OX-40, PD-1, IDO-1, FoxP3, CD163, and CTLA-4.

In another aspect of the present disclosure is a method of predicting a response to a PD-L1 targeted therapy by analyzing a PD-L1 positive tumor tissue sample for the presence or absence of tumor infiltrating PD-L1 positive immune cells comprising identifying immune cells that co-express PD-L1 and at least one CD marker, wherein the identifying of the immune cells that co-express PD-L1 and the at least one CD marker comprises contacting the tumor tissue sample with a first primary antibody specific for PD-L1 and contacting the tumor tissue sample with a second primary antibody specific for the at least one CD marker. In some embodiments, the method further comprises quantifying a number of PD-L1 positive tumor cells and quantifying a number of tumor infiltrating PD-L1 positive immune cells and optionally comparing the quantitated values, or any values derived therefrom, to control values or predetermined cut-off values as described herein. In some embodiments, the CD marker is selected from the group consisting of CD8, CD4, CD3, and CD45LCA. In some embodiments, the CD marker is CD45LCA.

In some embodiments, the method further comprises contacting the tissue sample with first and second detection reagents, wherein the first and second detection reagents comprise different substrates that effect deposition of different dyes. In some embodiments, each of the first and second detection reagents comprise (i) an enzyme, (ii) reagents for depositing the enzyme in proximity to the primary antibody when the primary antibody is bound to a tissue sample, and (iii) a substrate reactive with the enzyme to deposit a dye, wherein the first and second detection reagents comprise substrates that deposit different dyes. In some embodiments, the different substrates are selected to deposit a dye selected from the group consisting of DAB, DABSYL, DISCOVERY Purple, Cy5, and Rhodamine. In some embodiments, a first substrate deposits one of DISCOVERY Purple or DAB, and a second substrate deposits the other of DISCOVERY Purple or DAB. In some embodiments, a first substrate deposits one of DISCOVERY Purple or DABSYL, and a second substrate deposits the other of DISCOVERY Purple or DABSYL.

In some embodiments, the method further comprises contacting the tissue sample with at least one other detection probe specific for a tumor marker other than PD-L1 and detection reagents for detecting the at least one other detection probe. In other embodiments, the method comprises introducing, at least one other detection probe specific for EGFR, HER2, HPV, ALK, BRAF, OX-40, PD-1, IDO-1, FoxP3, CD 163, and CTLA-4.

In another aspect of the present disclosure includes a method of treating cancer in a patient comprising requesting a test providing the results of an analysis to determine whether a PD-L1 positive tumor tissue sample from the patient comprises tumor infiltrating PD-L1 positive lymphocytes and administering a PD-L1 targeted therapy to the patient if the patient's tumor tissue sample expresses PD-L1 positive tumor cells and tumor infiltrating PD-L1 positive lymphocytes, wherein the test comprises a multiplex assay wherein the tumor tissue sample is contacted with a first primary antibody specific for PD-L1 and a second primary antibody specific for at least one immune cell marker, wherein the tumor infiltrating PD-L1 positive lymphocytes co-express PD-L1 and the at least one immune cell marker. In some embodiments, the method further comprises quantifying a number of PD-L1 positive tumor cells and a number of tumor infiltrating PD-L1 positive immune cells, and optionally comparing the quantified values, or any values derived therefrom, to control values. In some embodiments, the immune cell marker is selected from the group consisting of CD8, CD4, CD3, and CD45LCA. In some embodiments, the immune cell marker is CD45LCA.

In some embodiments, the method further comprises contacting the tissue sample with first and second detection reagents, wherein the first and second detection reagents comprise different substrates that effect deposition of different dyes. In some embodiments, each of the first and second detection reagents comprise (i) an enzyme, (ii) reagents for depositing the enzyme in proximity to the primary antibody when the primary antibody is bound to a tissue sample, and (iii) a substrate reactive with the enzyme to deposit a dye on the sample, wherein the first and second detection reagents comprise substrate/enzyme combinations that result in deposition of different dyes. In some embodiments, the different substrates are selected to deposit a dye selected from the group consisting of DAB, DABSYL, DISCOVERY Purple, Cy5, and Rhodamine. In some embodiments, a first substrate deposits one of DISCOVERY Purple or DAB, and a second substrate deposits the other of DISCOVERY Purple or DAB. In some embodiments, a first substrate deposits one of DISCOVERY Purple or DABSYL, and a second substrate deposits the other of DISCOVERY Purple or DABSYL.

In some embodiments, the method further comprises contacting the tissue sample with at least one other detection probe specific for a tumor marker other than PD-L1 and detection reagents for detecting the at least one other detection probe. In other embodiments, the method comprises introducing, at least one other detection probe specific for EGFR, HER2, HPV, ALK, BRAF, OX-40, PD-1, IDO-1, FoxP3, CD 163, and CTLA-4. In some embodiments, the PD-L1 targeted therapy is Atezolizumab.

In another aspect of the present disclosure is method of differentiating PD-L1 positive tumor cells from PD-L1 positive immune cells comprising: (a) contacting a biological sample with a first detection probe specific for PD-L1; (b) contacting the biological sample with a first labeling conjugate that specifically binds to the first detection probe, wherein the first labeling conjugate comprises a first enzyme; (c) contacting the biological sample with a first signaling conjugate comprising a first latent reactive moiety and a first detectable moiety; (d) inactivating the first enzyme and, if the two primary antibodies are reactive with the same secondary antibody, denaturing and/or eluting the primary antibody; (e) contacting the biological sample with a second detection probe, where the second detection probe is specific for at least one immune cell marker; (f) contacting the biological sample with a second labeling conjugate that specifically binds to the second detection probe, wherein the second labeling conjugate comprises a second enzyme; (g) contacting the biological sample with a second signaling conjugate comprising a second latent reactive moiety and a second detectable moiety; (h) detecting signals from the first and second detectable moieties, wherein each of the first and second detectable moieties are each different, and wherein the PD-L1 positive immune cells co-express PD-L1 and the at least one immune cell marker. In some embodiments, the first detection probe is an anti-PD-L1 antibody; and the second detection probe is an anti-CD45LCA antibody. In some embodiments, first detectable moiety is one of diaminobenzidine or DISCOVERY Purple; and the second detectable moiety is the other of diaminobenzidine or DISCOVERY Purple. In some embodiments, method further comprises inactivating the second enzyme, contacting the biological sample with a third detection probe specific for a tumor marker other than PD-L1, contacting the sample with a third labeling conjugate that specifically binds to the third detection probe, wherein the third labeling conjugate comprises a third enzyme; and contacting the biological sample with a third signaling conjugate comprising a third latent reactive moiety and a third detectable moiety, wherein the third detectable moiety is different than either of the first or second detectable moieties.

In another aspect of the present disclosure is a method of identifying PD-L1 positive tumor cells, PD-L1 negative tumor cells, PD-L1 positive immune cells, and/or PD-L1 negative immune cells comprising (a) contacting a biological sample with a first detection probe, the first detection probe comprising a first primary antibody specific for one of PD-L1 or an immune cell marker; (b) contacting the biological sample with first detection reagents comprising a first enzyme; (c) inactivating the first enzyme; (d) contacting the biological sample with a second detection probe, the second detection probe comprising a second primary antibody selected from another of an antibody specific for another of PD-L1 or an immune cell marker; (e) contacting the biological sample with second detection reagents comprising a second enzyme; (f) detecting signals from the first and second detection reagents, wherein each of the first and second detection reagents comprise a different detectable moiety, and wherein the PD-L1 positive immune cells co-express PD-L1 and the immune cell marker. In some embodiments, the second detection probe is specific for lymphocytes. In some embodiments, the first detection probe is an anti-PD-L1 antibody; and the second detection probe is an anti-CD45LCA antibody. In some embodiments, the first detectable moiety is one of diaminobenzidine or DISCOVERY Purple; and the second detectable moiety is the other of diaminobenzidine or DISCOVERY Purple. In some embodiments, method further comprises inactivating the second enzyme, contacting the biological sample with a third detection probe specific for a tumor marker other than PD-L1, and contacting the sample with a third detection reagents.

Applicants have developed a multiplex assay and method for co-staining a tissue sample with a first detection probe specific for PD-L1 and at least a second detection probe specific for an immune cell marker. As compared with prior art methods, the multiplex assay and method developed by Applicants allows for an improved identification of PD-L1 positive immune cells, such as those infiltrating PD-L1 positive tumor tissues, and differentiation of PD-L1 positive immune cells from PD-L1 positive tumors cells. Again, and as compared with prior art methods, Applicants have demonstrated that the methods disclosed herein are superior and accurately allow for the identification of PD-L1 positive immune cells with enhanced throughput. Moreover, the methods disclosed herein, as compared with the prior art methods, are quicker, more accurate, and do not rely on the recognition of subtle morphological differences between PD-L1 positive cells immune cells and PD-L1 positive tumor cells. Indeed, it is believed that the methods disclosed herein remove some of the subjectivity associated with reading and differentiating between the different PD-L1 positive cell types, allowing for improved scoring and clinical diagnosis.

BRIEF DESCRIPTION OF THE DRAWINGS

The patent or application file contains at least one drawing executed in color. Copies of the patent or patent application publication with color drawing(s) will be provided by the Office upon request and payment of the necessary fee.

Non-limiting and non-exhaustive embodiments, are described with reference to the following drawings.

FIG. 3B provides an example of a tissue specimen where PD-L1 positive tumor cells are stained with Rhodamine (pink), tumor infiltrating lymphocytes are stained with DISCOVERY Purple (fuchsia), where those lymphocytes that co-express. PD-L1 appear red/navy.

FIG. 3C provides an example of a tissue specimen where PD-L1 positive tumor cells are stained with Rhodamine an appear pink (annotated with "a"), tumor infiltrating lymphocytes are stained with DISCOVERY Purple and appear fuchsia (annotated with "b"), where those lymphocytes that co-express PD-L1 appear red/navy (annotated with "c").

FIG. 4B provides an example of a tissue specimen where PD-L1 positive tumor cells are stained with DAB (brown), tumor infiltrating lymphocytes are stained with DISCOVERY Purple (fuchsia), where those lymphocytes that co-express PD-L1 appear are spotted with purple and brown.

FIG. 4C provides an example of a tissue specimen where PD-L1 positive tumor cells are stained with DAB and appear brown (annotated with "a"), tumor infiltrating lymphocytes are stained with DISCOVERY Purple and appear fuchsia (annotated with "b"), where those lymphocytes that co-express PD-L1 appear are spotted with purple and brown (annotated with "c").

DETAILED DESCRIPTION

Figure 1A:
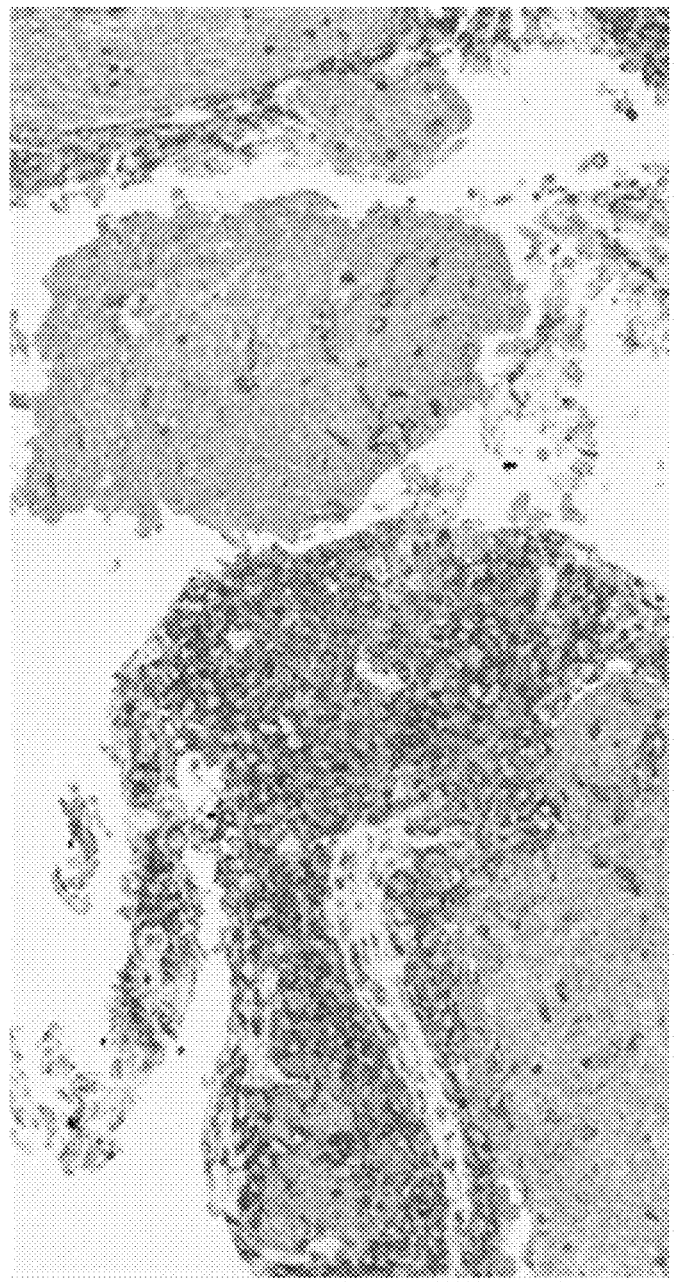
FIG. 1A provides an example of a tissue specimen where PD-L1 positive tumor cells are stained with DABSYL (yellow), tumor infiltrating lymphocytes are stained with DISCOVERY Purple (fuchsia), where those lymphocytes that co-express PD-L1 appear orange/red.
Figure 1B:
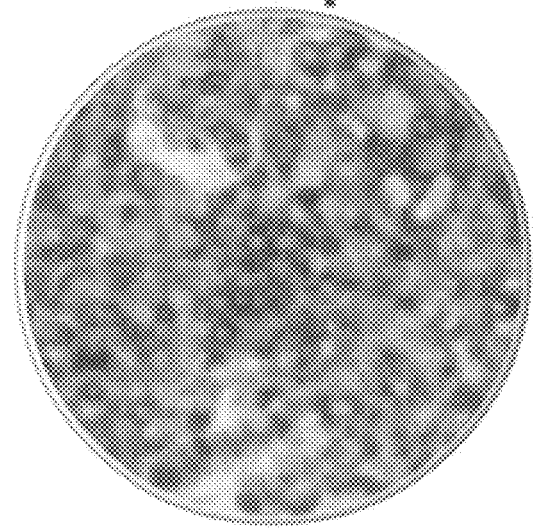
FIG. 1B provides an example of a tissue specimen where PD-L1 positive tumor cells are stained with DABSYL (yellow), tumor infiltrating lymphocytes are stained with DISCOVERY Purple (fuchsia), where those lymphocytes that co-express PD-L1 appear orange/red.
Figure 1B:
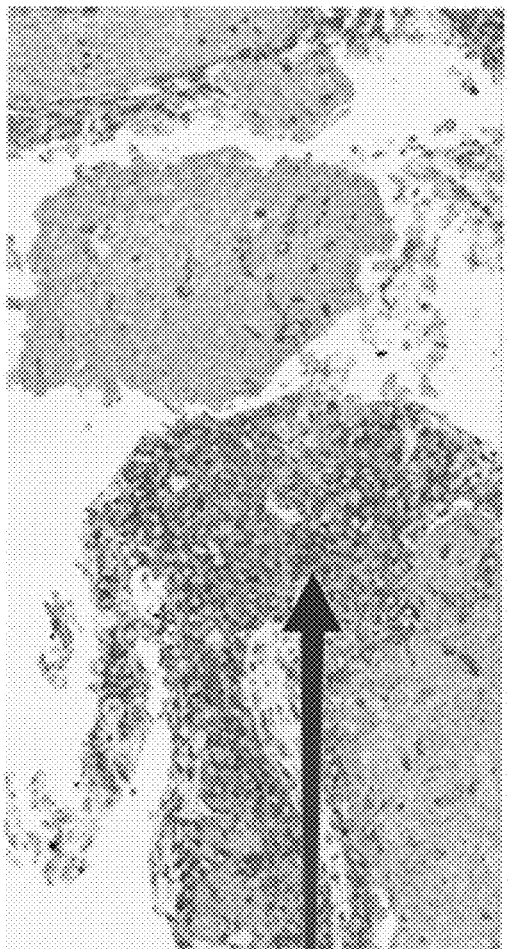
Figure 1C:
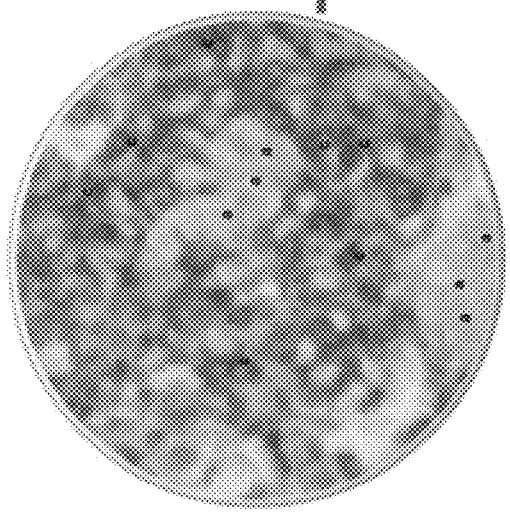
FIG. 1C provides an example of a tissue specimen where PD-L1 positive tumor cells are stained with DABSYL appear yellow (annotated with "a"), tumor infiltrating lymphocytes are stained with DISCOVERY Purple appear fuchsia (annotated with "b"), where those lymphocytes that co-express PD-L1 appear orange/red (annotated with "c").
Figure 1C:
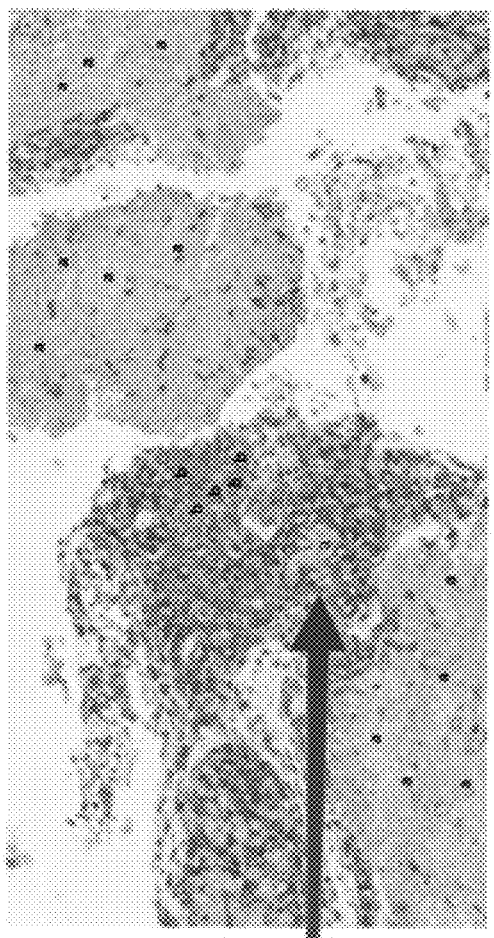
Figure 2A:
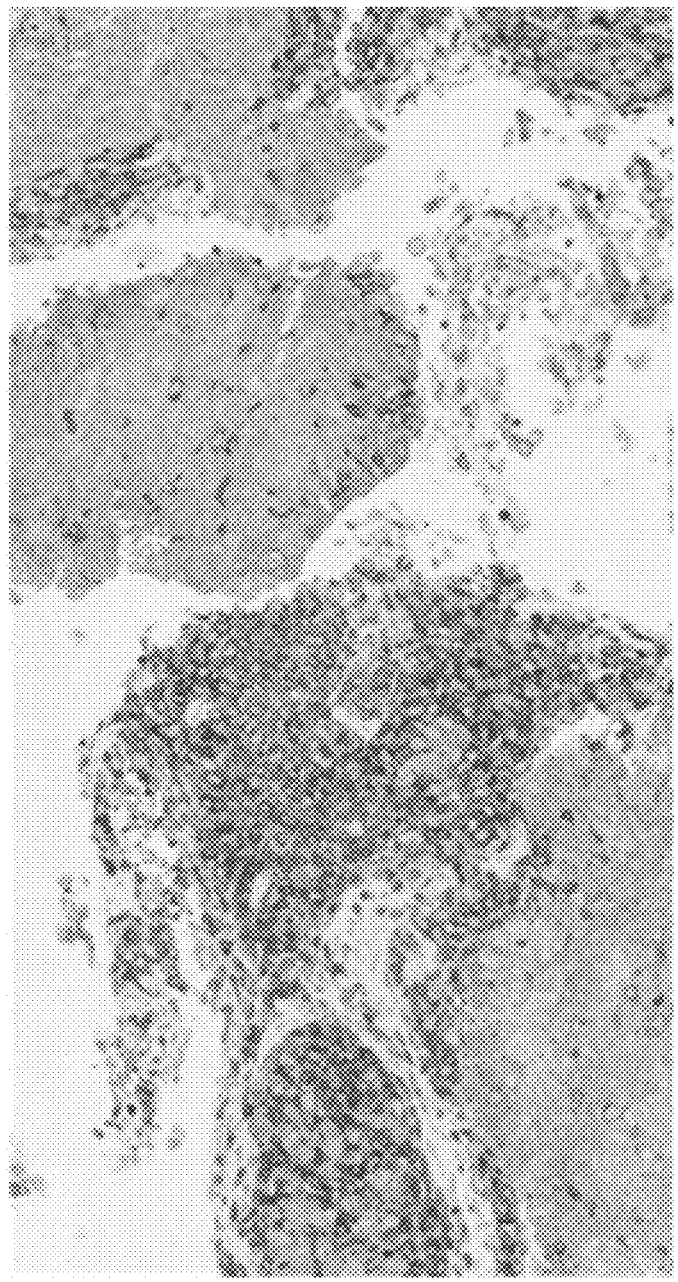
FIG. 2A provides examples of a tissue specimen where PD-L1 positive tumor cells are stained with Cy5 (cyan/blue), tumor infiltrating lymphocytes are stained with DISCOVERY Purple, (fuchsia), where those lymphocytes that co-express PD-L1 appear dark purple/navy.
Figure 2B:
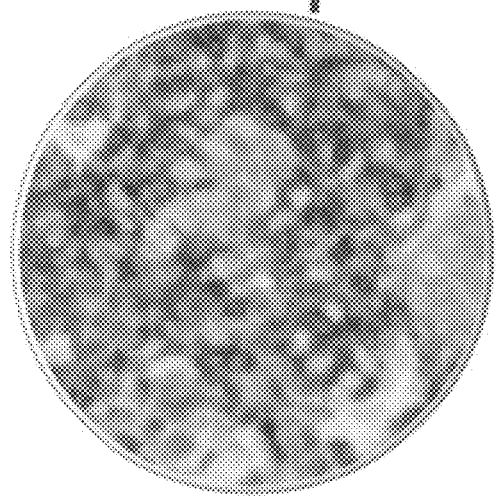
FIG. 2B provides examples of a tissue specimen where PD-L1 positive tumor cells are stained with Cy5 (cyan/blue), tumor infiltrating lymphocytes are stained with DISCOVERY Purple (fuchsia), where those lymphocytes that co-express PD-L1 appear dark purple/navy FIG. 2C provides examples of a tissue specimen where PD-L1 positive tumor cells are stained with Cy5 and appear cyan/blue (annotated with "a"), tumor infiltrating lymphocytes are stained with DISCOVERY Purple and appear fuchsia (annotated with "b"), where those lymphocytes that co-express PD-L1 appear dark purple/navy (annotated with "c").
Figure 2B:
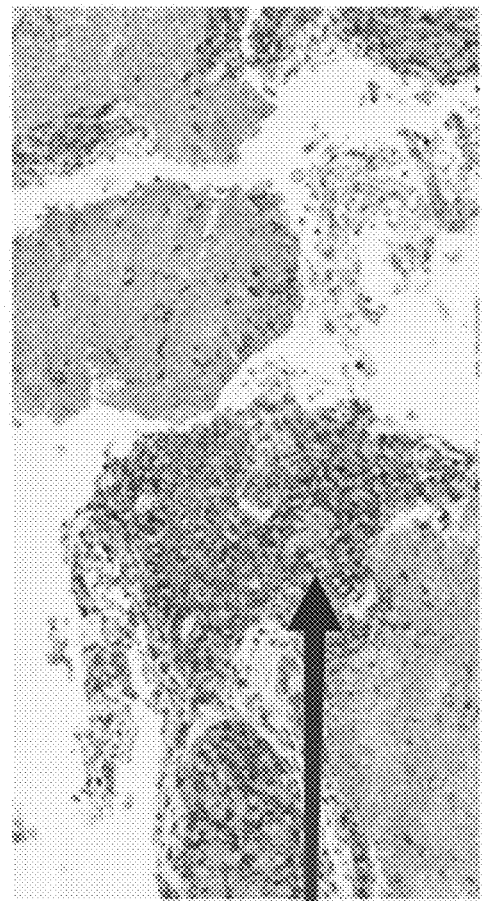
Figure 2C:
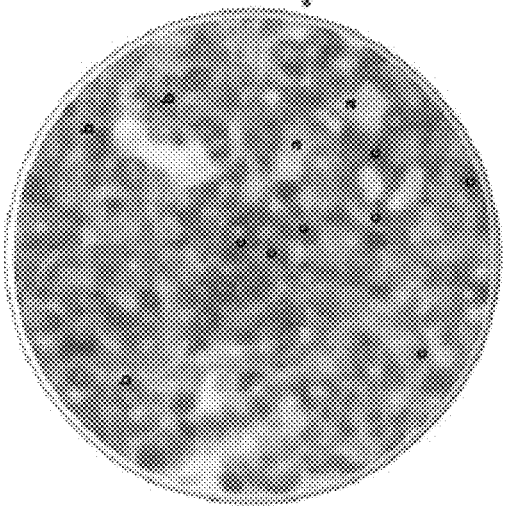
Figure 2C:
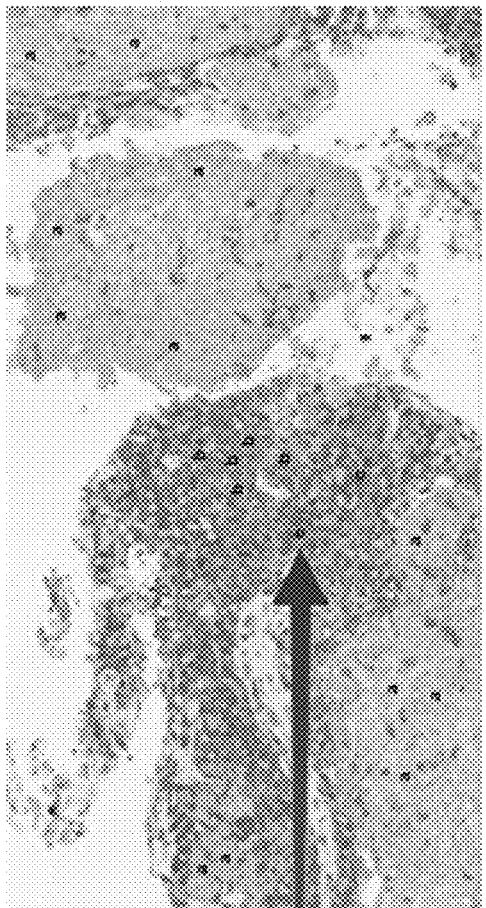
Figure 3A:
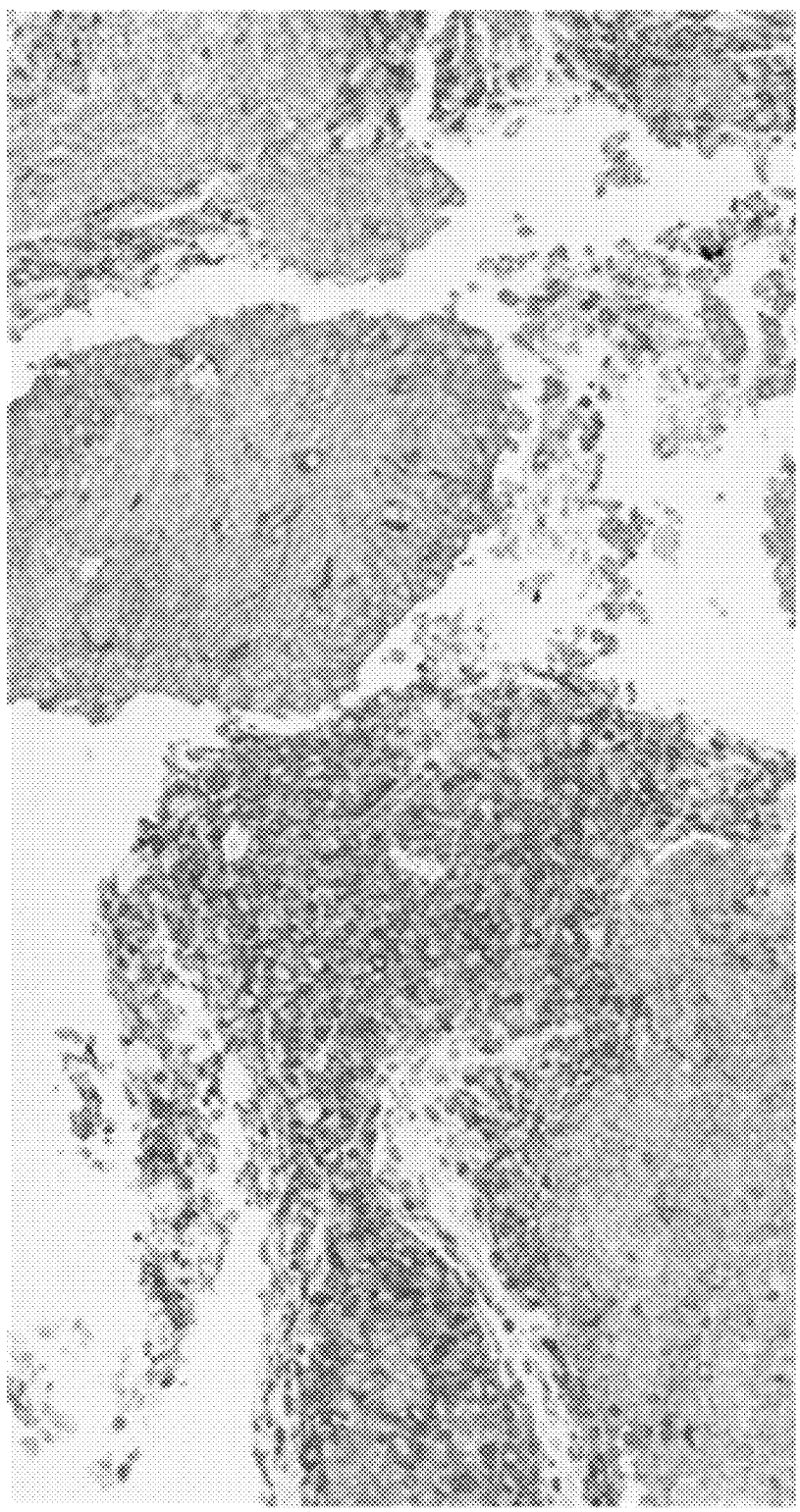
FIG. 3A provides an example of a tissue specimen where PD-L1 positive tumor cells are stained with Rhodamine (pink), tumor infiltrating lymphocytes are stained with DISCOVERY Purple (fuchsia), where those lymphocytes that co-express PD-L1 appear red/navy.

In general, the present disclosure is directed to multiplex assays, kits and methods, including automated methods, for identifying at PD-L1 positive immune cells and PD-L1 positive tumor cells in a tissue sample. In some embodiments, the multiplex assays, kits, and methods described herein allow a medical professional to distinguish between PD-L1 positive tumor cells, PD-L1 positive immune cells, and PD-L1 negative immune cells. In some embodiments, the multiplex assays, kits, and methods described herein may allow for a medical professional to assess whether a patient may benefit from treatment with a therapy targeting PD-L1, such as by detecting the presence and/or quantity of tumor infiltrating PD-L1 positive immune cells within a PD-L1 positive tumor tissue sample. In some embodiments, the multiplex assays, kits, and methods allow for the skilled artisan to clearly identify (i) a lymphocytic immune response, and (ii) a PD-L1 expression status of the tumor and infiltrating immune cells. These and other embodiments are described more fully herein.

As used herein, the singular terms "a," "an," and "the" include plural referents unless the context clearly indicates otherwise. Similarly, the word "or" is intended to include "and" unless the context clearly indicates otherwise.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein, the term "antibody," refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments (such as F(ab')2 fragments, Fab' fragments, Fab'-SH fragments and Fab fragments as are known in the art, recombinant antibody fragments (such as sFv fragments, dsFv fragments, bispecific sFv fragments, bispecific dsFv fragments, F(ab)'2 fragments, single chain Fv proteins ("scFv"), disulfide stabilized Fv proteins ("dsFv"), diabodies, and triabodies (as are known in the art), and camelid antibodies) that specifically bind to a molecule of interest (or a group of highly similar molecules of interest) to the substantial exclusion of binding to other molecules. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

"Antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins.

"Haprens" are small molecules that can combine specifically with an antibody, but typically are substantially incapable of being immunogenic except in combination with a carrier molecule. In some embodiments, haptens include, but are not limited to, pyrazoles (e.g. nitropyrazoles); nitrophenyl compounds; benzofurazans; triperpenes; ureas (e.g. phenyl ureas); thioureas (e.g. phenyl thioureas); rotenone and rotenone derivatives; oxazole (e.g. oxazole sulfonamides); thiazoles (e.g. thiazole sulfonamides); coumarin and coumarin derivatives; and cyclolignans. Additional non-limiting examples of haptens include thiazoles; nitroaryls; benzofurans; triperpenes; and cyclolignans. Specific examples of haptens include di-nitrophenyl, biotin, digoxigenin, and fluorescein, and any derivatives or analogs thereof. Other haptens are described in U.S. Pat. Nos. 8,846,320; 8,618,265; 7,695,929; 8,481,270; and 9,017,954, the disclosures of which are incorporated herein by reference in their entirety. The haptens themselves may be suitable for direct detection, i.e. they may give off a suitable signal for detection.

As used herein, the terms "sample" and "biological sample" shall refer to any composition containing or presumed to contain a biomarker. The term includes purified or separated components of cells, tissues, or blood, e.g., DNA, RNA, proteins, cell-free portions, or cell lysates. The sample can be a formalin-fixed, paraffin-embedded (FFPE) cellular sample, e.g., from a tumor or metastatic lesion. The sample can also be from frozen or fresh tissue, or from a liquid sample, e.g., blood or a blood component (plasma or serum), urine, semen; saliva, sputum, mucus, semen, tear, lymph, cerebral spinal fluid, material washed from a swab, etc. Samples also may include constituents and components of in vitro cultures of cells obtained from an individual, including cell lines. The sample can also be partially processed from a sample directly obtained from an individual, e.g., cell lysate or blood depleted of red blood cells.

As used herein, the term "cellular sample" refers to any sample containing intact cells, such as cell cultures, bodily fluid samples or surgical specimens taken for pathological, histological, or cytological interpretation.

As used herein, the term "tissue sample" shall refer to a cellular sample that preserves the cross-sectional spatial relationship between the cells as they existed within the subject from which the sample was obtained. "Tissue sample" shall encompass both primary tissue samples (i.e. cells and tissues produced by the subject) and xenografts (i.e. foreign cellular samples implanted into a subject).

As used herein, the term "cytological sample" refers to a cellular sample in which the cells of the sample have been partially or completely disaggregated, such that the sample no longer reflects the spatial relationship of the cells as they existed in the subject from which the cellular sample was obtained. Examples of cytological samples include tissue scrapings (such as a cervical scraping), fine needle aspirates, samples obtained by lavage of a subject, et cetera.

As used herein, "histochemical detection" refers to a process involving labelling a biomarker or other structures in a tissue sample with detection reagents in a manner that permits microscopic detection of the biomarker or other structures in the context of the cross-sectional relationship between the structures of the tissue sample. Examples include immunohistochemistry (IHC), chromogenic in situ hybridization (CISH), fluorescent in situ hybridization (FISH), silver in situ hybridization (SISH), and hematoxylin and eosin (H&E) staining of formalin-fixed, paraffin-embedded tissue sections.

As used herein, "cytochemical detection" refers to a process involving labelling a biomarker or other structures in a cytological sample with detection reagents in a manner that permits microscopic detection of the biomarker or other structures in the context of the cells of the cytological sample.

As used herein, the term "section" shall refer to a thin slice of a tissue sample suitable for microscopic analysis, typically cut using a microtome.

As used herein, the term "serial section" shall refer to any one of a series of sections cut in sequence from a tissue sample. For two sections to be considered "serial sections" of one another, they do not necessarily need to consecutive sections from the tissue, but they should generally contain the same tissue structures in the same cross-sectional relationship, such that the structures can be matched to one another after histological staining.

As used herein, the phrase "specific binding," "specifically binds to," or "specific for" refers to measurable and reproducible interactions such as binding between a target and a biomarker-specific agent, which is determinative of the presence of the target in the presence of a heterogeneous population of molecules including biological molecules. For example, a binding entity that specifically binds to a target is an antibody that binds this target with greater affinity, avidity, more readily, and/or with greater duration than it binds to other targets. In one embodiment, the extent of binding of a binding entity to an unrelated target is less than about 10% of the binding of the antibody to the target as measured, e.g., by a radioimmunoassay (RIA). In certain embodiments, a binding entity that specifically binds to a target has a dissociation constant (Kd) of ≤1 µM, ≤100 nM, ≤10 nM, ≤1 nM, or ≤0.1 nM. In another embodiment, specific binding can include, but does not require exclusive binding.

As used herein, "detection probe" shall refer to any compound or composition that binds to a specific structure within a sample in a manner that permits detection of the structure in the sample. Examples include:

nucleic acid probes capable of specifically hybridizing to particular nucleotide sequences;
nucleic acid primer sets capable of amplifying a specific nucleotide sequence or set of sequences when paired with appropriate amplification reagents;
antibodies and antigen binding fragments thereof; and
engineered specific binding structures, including ADNECTINs (scaffold based on 10th FN3 fibronectin; Bristol-Myers-Squibb Co.), AFFIBODYs (scaffold based on Z domain of protein A from *S. aureus;* Affibody AB, Solna, Sweden), AVIMERs (scaffold based on domain A/LDL receptor; Amgen, Thousand Oaks, CA), dAbs (scaffold based on VH or VL antibody domain; GlaxoSmithKline PLC, Cambridge, UK), DARPins (scaffold based on Ankyrin repeat proteins; Molecular Partners AG, Zürich, CH), ANTICALINs (scaffold based on lipocalins; Pieris AG, Freising, DE), NANOBODYs (scaffold based on VHH (camelid Ig); Ablynx N/V, Ghent, BE); TRANS-BODYs (scaffold based on Transferrin; Pfizer Inc., New York, NY), SMIPs (Emergent Biosolutions, Inc., Rockville, MD), and TETRANECTINS (scaffold based on C-type lectin domain (CTLD), tetranectin; Borean Pharma A/S, Aarhus, DK) (Descriptions of such engineered specific binding structures are reviewed by Wurch et al., *Development of Novel Protein Scaffolds as Alternatives to Whole Antibodies for Imaging and Therapy: Status on Discovery Research and Clinical Validation,* Current Pharmaceutical Biotechnology, Vol. 9, pp. 502-509 (2008), the content of which is incorporated by reference).

The detection probes may include a label for direct detection, such as radioactive isotopes, enzymes, enzyme substrates, co-factors, ligands, chemiluminescent or fluorescent agents, haptens (including, but not limited to, DNP), and enzymes. Alternatively, the detection probes may contain no label or tag and may be detected indirectly (e.g. with a secondary antibody or other molecules that specifically associate the detection probe with a label or tag).

"Multiplex," "multiplexed," or "multiplexing" refers to detecting multiple targets in a sample concurrently, substantially simultaneously, or sequentially. Multiplexing can include identifying and/or quantifying multiple distinct nucleic acids (e.g., DNA, RNA, mRNA, miRNA) and polypeptides (e.g., proteins) both individually and in any and all combinations.

The term "primary detection probe" or "primary antibody" refers to ε detection probe or an antibody which binds specifically to a target protein antigen in a tissue sample. A primary detection probe is generally the first detection used in a histochemical procedure.

The term "secondary detection probe" or "secondary antibody" herein refers to an antibody which binds specifically to a detection probe or portion thereof (e.g. a hapten or a primary antibody), thereby forming a bridge between the detection probe and a subsequent reagent (e.g. a label, an enzyme, etc.), if any. A secondary antibody may be used to indirectly detect detection probes.

"PD-L1 tumor cells" means those tumor cells, including metastatic cells, which express or overexpress PD-L1.

"Target" means any molecule for which the presence, location and/or concentration is or can be determined. Examples of targets include nucleic acid sequences and proteins, such as those disclosed herein and, in particular, include PD-L1 and immune cell markers (cluster of differentiation ("CD") markers).

Tumor infiltrating lymphocytes ("TILs") are a type of immune cell found in tumors and are implicated in "killing" of tumor cells.

Primary Detection Probes

The multiplex assays, kits, and methods of the present disclosure comprise at least two detection probes, namely detection probes which enable detection of at least (i) PD-L1 positive tumor cells, and (ii) immune cells. Of course, the skilled artisan will recognize that additional detection probes may be combined with the at last two detection probes to effectuate detection of other targets, including other tumor markers. While certain embodiments herein refer to primary antibodies as detection probes for use in IHC, other protein specific detection probes for use in histochemical assays and nucleic acid probes for use in in situ hybridization assays may also be equally utilized.

In some embodiments, the detection probes utilized are primary antibodies, namely primary antibodies which enable detection of PD-L1 positive tumor cells and immune cells. In some embodiments, the detection probes include primary antibodies specific to PD-L1 (e.g. anti-PD-L1 antibodies). In an embodiment, the PD-L1 antibodies are immunospecific for a polypeptide comprising SEQ ID NO: 1. In other embodiments, the detection probes are primary antibodies that are specific to at least tumor cells that express PD-L1. In yet other embodiments, the detection probes are primary antibodies that are specific to PD-1. Anti-PD-L1 antibodies are available, for example, from Ventana Medical Systems, Tucson Ariz.; and include SP142 (a rabbit monoclonal IHC antibody) and SP263 (a rabbit monoclonal IHC antibody). Other anti-PD-L1 antibodies are available from Dako North America (Carpinteria, CA) and include PD-L1 IHC 22C3 pharmDx and PD-L1 IHC 28-8 pharmDx. SP142 is described in detail in US20160009805A1, and SP263 is describe in detail in US20150346208A1, the content of each of which is incorporated by reference in its entirety. SP142 and SP263 include the following heavy and light chain sequences:

TABLE 1

| | Heavy Chain immunoglobulin variable domain sequence | LC immunoglobulin variable domain sequence (kappa) |
|---|---|---|
| SP142 | QSLEESGGRLVKPDETLTITCTVSGIDLS SNGLTWVRQAPGEGLEWIGTINKDASA YYASWAKGRLTISKPSSTKVDLKITSPT TEDTATYFCGRIAFKTGTSIWGPGTLVT VSS (SEQ ID NO: 2) | AIVMTQTPSPVSAAVGGTVTINCQ ASESVYSNNYLSWFQQKPGQPPK LLIYLASTLASGVPSRFKGSGSGTQ FTLTISGVQCDDAATYYCIGGKSS STDGNAFGGGTEVVVR (SEQ ID NO: 3) |
| SP263 | QSLEESGQRLVTPGTPLTLTCTASGFSLS NHAISWVRQAPGKGLEWIGTINSDTHT YYATWPKGRFTISKTSSTTVDLKMTSPT TEDTATYFCARRIFSSSNIWGPGTLVTV SS (SEQ ID NO: 4) | AIVMTQTSSPVSAVVGGTVAINCQ ASQSIYNNNWLSWFQQKPGQPPK LLIYLASTLASGVPSRFKGSGSGTQ FTLTISDVVCDDAATYYCIGGESS NNDGIAFGGGTEVVVK (SEQ ID NO: 5) |

In some embodiments, the detection probes utilized are specific for immune cell markers. In some embodiments, the detection probes are selected from primary antibodies that are specific for markers of lymphocytes, including T lymphocytes and B lymphocytes. In other embodiments, the detection probes are selected from primary antibodies that are specific for markers of leukocytes, T-helper cells, T-regulatory cells, and/or cytotoxic T cells. In yet other embodiments, the detection probes are selected from primary antibodies that are specific for a broad spectrum lymphocyte secondary biomarker.

In some embodiments, the detection probes are selected from primary antibodies that are specific for certain receptors and/or ligands including, but not limited to, CD45, CD45LCA (where 'LCA' refers to leukocyte common antigen) CD3, CD4, CD8, CD20, CD 25, CD19 and CD163 (e.g. anti-CD antibodies). In other embodiments, the detection probe is a primary antibody that is specific for CD45LCA. In some embodiments, the detection probe is anti-CD45LCA primary antibody, such as available from Ventana Medical Systems, Tucson, Ariz., and available under the brand name CONFIRM anti-CD45, LCA (RP2/18) (a mouse monoclonal antibody (IgG1) that specifically binds to antigens located on the membranes of leukocytes).

Detection Reagents

The detection reagents are selected to effect deposition of a detectable moiety in proximity to the detection reagents when bound to a tissue sample. A "detectable moiety" is a molecule or material that can produce a detectable signal (such as visually, electronically or otherwise) that indicates the presence (i.e. qualitative analysis) and/or concentration (i.e. quantitative analysis) of the targets in a sample. A detectable signal can be generated by any known or yet to be discovered mechanism including absorption, emission and/or scattering of a photon (including radio frequency, microwave frequency, infrared frequency, visible frequency and ultra-violet frequency photons). In some embodiments, the detectable moiety includes chromogenic, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity). In some examples, the detectable moiety is a fluorophore, which belongs to several common chemical classes including coumarins, fluoresceins (or fluorescein derivatives and analogs), rhodamines, resorufins, luminophores and cyanines. Additional examples of fluorescent molecules can be found in Molecular Probes Handbook—A Guide to Fluorescent Probes and Labeling Technologies, Molecular Probes, Eugene, Oreg., TheroFisher Scientific, 11$^{th}$ Edition. In other embodiments, the detectable moiety is a detectable via brightfield microscopy. In a specific embodiment, the detectable moiety comprises a dye elected from the group consisting of diaminobenzidine (DAB), 4-(dimethylamino) azobenzene-4'-sulfonamide (DABSYL), tetramethylrhodamine (DISCOVERY Purple), N,N'-biscarboxypentyl-5,5'-disulfonato-indo-dicarbocyanine (Cy5), and Rhodamine 110 (Rhodamine).

In some embodiments, the detectable moiety is directly conjugated to the detection probe, and thus is deposited on the sample upon binding of the detection probe to its target. In other cases, deposition of the detectable moiety is effected by an enzymatic reaction. In some embodiments, suitable enzymes include, but are not limited to, horseradish peroxidase, alkaline phosphatase, acid phosphatase, glucose oxidase, β-galactosidase, β-glucuronidase or β-lactamase. In other embodiments, enzymes include oxidoreductases, hydrolase, or peroxidases (e.g. HRP or AP). The enzyme may be directly conjugated to the detection probe, or may be indirectly associated with the detection probe via a labeling conjugate. As used herein, a "labeling conjugate" comprises: (a) a specific binding entity that is specific for a primary specific binding entity or for another entity that is linked to or associated with the primary antibody (such as a secondary antibody bound to the primary antibody or a hapten linked to the primary antibody, or the like); and (b) an enzyme linked to the specific binding entity, wherein the enzyme is reactive with the chromogenic substrate, signaling conjugate, or enzyme-reactive dye under appropriate reaction conditions to effect in situ generation of the dye and/or deposition of the dye on the tissue sample.

In some cases, the enzyme reacts with a chromogenic compound/substrate. Particular non-limiting examples of chromogenic compounds/substrates include 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-∠-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-∠-chloro-3-indolyl-β-D-glucuronide (X-Gluc), 3-amino-9-ethyl carbazol (AEC), fuchsin, iodonitrotetrazolium (INT), tetrazolium blue, or tetrazolium violet.

In some embodiments, the enzyme can be used in a metallographic detection scheme. Metallographic detection methods include using an enzyme such as alkaline phosphatase in combination with a water-soluble metal ion and a redox-inactive substrate of the enzyme. In some embodiments, the substrate is converted to a redox-active agent by the enzyme, and the redox-active agent reduces the metal ion, causing it to form a detectable precipitate. (See, for example, U.S. patent application Ser. No. 11/015,646, filed Dec. 20, 2004, PCT Publication No. 2005/003777 and U.S. Patent Application Publication No. 2004/0265922; each of which is incorporated by reference herein in its entirety). Metallographic detection methods include using an oxidoreductase enzyme (such as horseradish peroxidase) along with a water soluble metal ion, an oxidizing agent and a reducing agent, again to for form a detectable precipitate. (See, for example, U.S. Pat. No. 6,670,113, which is incorporated by reference herein in its entirety).

In some embodiments, the enzymatic action occurs between the enzyme and the dye itself, wherein the reaction converts the dye from a non-binding species to a species deposited on the sample. For example, reaction of DAB with a peroxidase (such as horseradish peroxidase).oxidizes the DAB, causing it to precipitate.

In yet other embodiments, the dye is deposited via a signaling conjugate comprising a latent reactive moiety configured to react with the enzyme to form a reactive species that can bind to the sample or to other detection components. These reactive species are capable of reacting with the sample proximal to their generation, i.e. near the enzyme, but rapidly convert to a non-reactive species so that the signaling conjugate is not deposited at sites distal from the site at which the enzyme is deposited. Examples of latent reactive moieties include: quinone methide (QM) analogs, such as those described at WO2015124703A1, and tyramide conjugates, such as those described at, WO2012003476A2, each of which is hereby incorporated by reference herein in its entirety. In some examples, the signaling conjugate includes a latent reactive moiety directly conjugated to a dye, such as N,N'-biscarboxypentyl-5,5'-disulfonato-indo-dicarbocyanins (Cy5), 4-(dimethylamino) azobenzene-4'-sulfonamide (DABSYL), tetramethylrhodamine (DISCO Purple), and Rhodamine 110 (Rhodamine). In other examples, the latent reactive moiety is linked to one member of a specific binding pair, and the dye is linked to the other member of the specific binding pair. In other examples, the latent reactive moiety is linked to one member of a specific binding pair, and an enzyme is linked to the other member of the specific binding pair, wherein the enzyme is (a) reactive with a chromogenic substrate to, effect generation of the dye, or (b) reactive with a dye to effect deposition of the dye (such as DAB). Examples of specific binding pairs include:

(1) a biotin or a biotin derivative (such as desthiobiotin) linked to the latent reactive moiety, and a biotin-binding entity (such as avidin, streptavidin, deglycosylated avidin (such as NEUTRAVIDIN), or a biotin binding protein having a nitrated tyrosine at its biotin binding site (such as CAPTAVIDIN)) linked to a dye or to an enzyme reactive with a chromogenic substrate or reactive with a dye (for example, a peroxidase linked to the biotin-binding protein when the dye is DAB); and (2) a hapten linked to the latent reactive moiety, and an anti-hapten antibody linked to a dye or to an enzyme reactive with a chromogenic substrate or reactive with a dye (for example, a peroxidase linked to the biotin-binding protein when the dye is DAB).

In some embodiments, the detection reagents utilized in the multiplex assays, kits, and methods include dyes and reagents useful for deposition of the dye onto the tissue sample. As such, in some embodiments, detection reagents comprise a labeling conjugate, and further comprise one of a chromogenic substrate, a signaling conjugate, or an enzyme-reactive dye. In other embodiments, detection reagents comprise a labeling conjugate, and further comprise one of a chromogenic substrate, a signaling conjugate, or an enzyme-reactive dye.

Specific arrangements of primary detection probes and detection reagents include those set forth in Table 2. As would be appreciated by a person having ordinary skill in the art, the detection for each of the primary antibodies may be the same, or it may be different.

TABLE 2

| A. Primary detection probe linked directly to detectable moiety | |
|---|---|
| 1° detection probe-Dye | |
| B. Primary detection probe linked to enzyme reacting with detectable moiety | |
| 1° detection probe-Enzyme + DAB | |
| 1° detection probe-Enzyme + Chromogen | |
| C. Primary detection probe linked to Enzyme reacting with signaling moiety | |
| C1. Signaling Moiety comprises detectable moiety | 1° detection probe-Enzyme + QM-Dye |
| | 1° detection probe-Enzyme + Tyramide-Dye |
| C2. Signaling moiety comprises enzyme that reacts directly with detectable moiety | 1° detection probe-Enzyme + QM-Enzyme + DAB |
| | 1° detection probe-Enzyme + QM-Enzyme + Chromogen |
| | 1° detection probe-Enzyme + Tyramide-Enzyme + DAB |
| | 1° detection probe-Enzyme + Tyramide-Enzyme + Chromogen |
| C3. Signaling moiety comprises enzyme that reacts with second signaling moiety comprising detectable moiety | 1° detection probe-Enzyme + QM-Enzyme + QM + Dye |
| | 1° detection probe-Enzyme + QM-Enzyme + Tyramide-Dye |
| | 1° detection probe-Enzyme + Tyramide-Enzyme + QM-Dye |
| | 1° detection probe-Enzyme + Tyramide-Enzyme Tyramide-Dye |

TABLE 2-continued

| | |
|---|---|
| C4. Signaling moiety comprises member of a specific binding pair and other member of binding pair is linked to detectable moiety | 1° detection probe-Enzyme + Tyramide-(biotin/hapten) + Dye-(avidin/anti-hapten detection probe)<br>1° detection probe-Enzyme + QM-(biotin/hapten) + Dye-(avidin/anti-hapten detection probe) |
| C5. Signaling moiety comprises member of a specific binding pair and other member of binding pair is linked to enzyme reactive with detectable moiety | 1° detection probe-Enzyme + QM-(biotin/hapten) + Enzyme-(avidin/anti-hapten detection probe) + DAB<br>1° detection probe-Enzyme + QM-(biotin/hapten) + Enzyme-(avidin/anti-hapten detection probe) + Chromogen<br>1° detection probe-Enzyme + Tyramide--(biotin/hapten) + Enzyme-(avidin/anti-hapten detection probe) + DAB<br>1° detection probe-Enzyme + Tyramide-(biotin/hapten) + Enzyme-(avidin/anti-hapten detection probe) + Chromogen |
| C6. Signaling moiety comprises member of a specific binding pair and other member of binding pair is linked to enzyme reactive with second signaling moiety linked to a detectable moiety | 1° detection probe-Enzyme + QM-(biotin/hapten) + Enzyme-(avidin/anti-hapten detection probe) + Tyramide-Dye<br>1° detection probe-Enzyme + QM-(biotin/hapten) + Enzyme-(avidin/anti-hapten detection probe) + QM-Dye<br>1° detection probe-Enzyme + Tyramide-(biotin/hapten) + Enzyme-(avidin/anti-hapten detection probe) + Tyramide-Dye<br>1° detection probe-Enzyme + Tyramide-(biotin/hapten) + Enzyme-(avidin/anti-hapten detection probe) + QM-Dye |
| D. Primary linked to member of specific binding pair | |
| D1. Dye linked to other member of specific binding pair | 1° detection probe-(biotin/hapten) + Dye-(avidin/anti-hapten detection probe) |
| D2. Enzyme linked to other member of specific binding pair, wherein the enzyme is reactive with detectable moiety | 1° detection probe-(biotin/hapten) + Enzyme-(avidin/anti-hapten detection probe) + DAB<br>1° detection probe-(biotin/hapten) + Enzyme-(avidin/anti-hapten detection probe) + Chromogen<br>1° detection probe-(biotin/hapten) + Enzyme-(avidin/anti-hapten detection probe) + QM-Dye<br>1° detection probe-(biotin/hapten) + Enzyme-(avidin/anti-hapten detection probe) + Tyramide-Dye |
| E. Secondary detection probe linked directly to detectable moiety | |
| | 1° detection probe + 2° detection probe-Dye |
| F. Secondary detection probe linked to Enzyme reacting with detectable moiety | |
| | 1° detection probe + 2° detection probe-Enzyme + DAB<br>1° detection probe + 2° detection probe-Enzyme + Chromogen |
| G. Secondary detection probe linked to Enzyme reacting with signaling moiety | |
| G1. Signaling Moiety comprises detectable moiety | 1° detection probe + 2° detection probe-Enzyme + QM-Dye<br>1° detection probe + 2° detection probe-Enzyme + Tyramide-Dye |
| G2. Signaling moiety comprises enzyme that reads directly with detectable moiety | 1° detection probe + 2° detection probe-Enzyme + QM-Enzyme + DAB<br>1° detection probe + 2° detection probe-Enzyme + QM-Enzyme + Chromogen<br>1° detection probe + 2° detection probe-Enzyme + Tyramide-Enzyme + DAB<br>1° detection probe + 2° detection probe-Enzyme + Tyramide-Enzyme + Chromogen |
| G3. Signaling moiety comprises enzyme that reacts with second signaling moiety comprising detectable moiety | 1° detection probe + 2° detection probe-Enzyme + QM-Enzyme + QM-Dye<br>1° detection probe + 2° detection probe-Enzyme + QM-Enzyme + Tyramide-Dye<br>1° detection probe + 2° detection probe-Enzyme + Tyramide-Enzyme + QM-Dye<br>1° detection probe + 2° detection probe-Enzyme + Tyramide-Enzyme + Tyramide-Dye |
| G4. Signaling moiety comprises member of a specific binding pair and | 1° detection probe + 2° detection probe-Enzyme + Tyramide-(biotin/hapten) + Dye-(avidin/anti-hapten detection probe) |

TABLE 2-continued

| | |
|---|---|
| other member of binding pair is linked to detectable moiety | 1° detection probe + 2° detection probe-Enzyme + QM-(biotin/hapten) + Dye-(avidin/anti-hapten detection probe) |
| G5. Signaling moiety comprises member of a specific binding pair and other member of binding pair is linked to enzyme reactive with detectable moiety | 1° detection probe + 2° detection probe-Enzyme + QM-(biotin/hapten) + Enzyme-(avidin/anti-hapten detection probe) + DAB |
| | 1° detection probe + 2° detection probe-Enzyme + QM-(biotin/hapten) + Enzyme-(avidin/anti-hapten detection probe) + Chromogen |
| | 1° detection probe + 2° detection probe-Enzyme + Tyramide-(biotin/hapten) + Enzyme-(avidin/anti-hapten detection probe) + DAB |
| | 1° detection probe + 2° detection probe-Enzyme + Tyramide-(biotin/hapten) + Enzyme-(avidin/anti-hapten detection probe) + Chromogen |
| G6. Signaling moiety comprises member of a specific binding pair and other member of binding pair is linked to enzyme reactive with second signaling moiety linked to a detectable moiety | 1° detection probe + 2° detection probe-Enzyme + QM-(biotin/hapten) + Enzyme-(avidin/anti-hapten detection probe) + Tyramide-Dye |
| | 1° detection probe + 2° detection probe-Enzyme + QM-(biotin/hapten) + Enzyme-(avidin/anti-hapten detection probe) + QM-Dye |
| | 1° detection probe + 2° detection probe-Enzyme + Tyramide-(biotin/hapten) + Enzyme-(avidin/anti-hapten detection probe) + Tyramide-Dye |
| | 1° detection probe + 2° detection probe-Enzyme + Tyramide-(biotin/hapten) + Enzyme-(avidin/anti-hapten detection probe) + QM-Dye |
| H. Secondary detection probe linked to member of specific binding pair | |
| H1. Dye linked to other member of specific binding pair | 1° detection probe + 2° detection probe-(biotin/hapten) + Dye-(avidin/anti-hapten detection probe) |
| H2. Enzyme linked to other member of specific binding pair, wherein the enzyme is reactive with detectable moiety | 1° detection probe + 2° detection probe-(biotin/hapten) + Enzyme-(avidin/anti-hapten detection probe) + DAB |
| | 1° detection probe + 2° detection probe-(biotin/hapten) + Enzyme-(avidin/anti-hapten detection probe) + Chromogen |
| | 1° detection probe + 2° detection probe-(biotin/hapten) + Enzyme-(avidin/anti-hapten detection probe) + QM-Dye |
| | 1° detection probe + 2° detection probe-(biotin/hapten) + Enzyme-(avidin/anti-hapten detection probe) + Tyramide-Dye |
| I. Tertiary detection probe linked directly to detectable moiety | |
| | 1° detection probe + 2° detection probe + 3° detection probe-Dye |
| J. Tertiary detection probe linked to Enzyme reacting with detectable moiety | |
| | 1° detection probe + 2° detection probe + 3° detection probe-Enzyme + DAB |
| | 1° detection probe + 2° detection probe + 3° detection probe-Enzyme + Chromogen |
| K. Tertiary detection probe linked to Enzyme reacting with signaling moiety | |
| K1. Signaling Moiety comprises detectable moiety | 1° detection probe + 2° detection probe + 3° detection probe-Enzyme + QM-Dye |
| | 1° detection probe + 2° detection probe + 3° detection probe-Enzyme + Tyramide-Dye |
| K2. Signaling moiety comprises enzyme that reacts directly with detectable moiety | 1° detection probe + 2° detection probe + 3° detection probe-Enzyme + QM-Enzyme + DAB |
| | 1° detection probe + 2° detection probe + 3° detection probe-Enzyme + QM-Enzyme + Chromogen |
| | 1° detection probe + 2° detection probe + 3° detection probe-Enzyme + Tyramide-Enzyme + DAB |
| | 1° detection probe + 2° detection probe + 3° detection probe-Enzyme + Tyramide-Enzyme + Chromogen |
| K3. Signaling moiety comprises enzyme that reads with second signaling moiety comprising detectable moiety | 1° detection probe + 2° detection probe + 3° detection probe-Enzyme + QM-Enzyme + QM-Dye |
| | 1° detection probe + 2° detection probe + 3° detection probe-Enzyme + QM-Enzyme + Tyramide-Dye |
| | 1° detection probe + 2° detection probe + 3° detection probe-Enzyme + Tyramide-Enzyme + QM-Dye |

TABLE 2-continued

| | |
|---|---|
| | 1° detection probe + 2° detection probe + 3° detection probe-Enzyme + Tyramide-Enzyme + Tyramide-Dye |
| K4. Signaling moiety comprises member of a specific binding pair and other member of binding pair is linked to detectable moiety | 1° detection probe + 2° detection probe + 3° detection probe-Enzyme + Tyramide-(biotin/hapten) + Dye-(avidin/anti-hapten detection probe) |
| | 1° detection probe + 2° detection probe + 3° detection probe-Enzyme + QM-(biotin/hapten) + Dye-(avidin/anti-hapten detection probe) |
| K5. Signaling moiety comprises member of a specific binding pair and other member of binding pair is linked to enzyme reactive with detectable moiety | 1° detection probe + 2° detection probe + 3° detection probe-Enzyme + QM-(biotin/hapten) + Enzyme-(avidin/anti-hapten detection probe) + DAB |
| | 1° detection probe + 2° detection probe + 3° detection probe-Enzyme + QM-(biotin/hapten) + Enzyme-(avidin/anti-hapten detection probe) + Chromogen |
| | 1° detection probe + 2° detection probe + 3° detection probe-Enzyme + Tyramide-(biotin/hapten) + Enzyme-(avidin/anti-hapten detection probe) + DAB |
| | 1° detection probe + 2° detection probe + 3° detection probe-Enzyme + Tyramide-(biotin/hapten) + Enzyme-(avidin/anti-hapten detection probe) + Chromogen |
| K6. Signaling moiety comprises member of a specific binding pair and other member of binding pair is linked to enzyme reactive with second signaling moiety linked to a detectable moiety | 1° detection probe + 2° detection probe + 3° detection probe-Enzyme + QM-(biotin/hapten) + Enzyme-(avidin/anti-hapten detection probe) + Tyramide-Dye |
| | 1° detection probe + 2° detection probe + 3° detection probe-Enzyme + QM-(biotin/hapten) + Enzyme-(avidin/anti-hapten detection probe) + QM-Dye |
| | 1° detection probe + 2° detection probe + 3° detection probe-Enzyme + Tyramide-(biotin/hapten) + Enzyme-(avidin/anti-hapten detection probe) + Tyramide-Dye |
| | 1° detection probe + 2° detection probe + 3° detection probe-Enzyme + Tyramide-(biotin/hapten) + Enzyme-(avidin/anti-hapten detection probe) + QM-Dye |
| L. Tertiary detection probe linked to member of specific binding pair | |
| L1. Dye linked to other member of specific binding pair | 1° detection probe + 2° detection probe + 3° detection probe-(biotin/hapten) + Dye-(avidin/anti-hapten detection probe) |
| L2. Enzyme linked to other member of specific binding pair, wherein the enzyme is reactive with detectable moiety | 1° detection probe + 2° detection probe + 3° detection probe-(biotin/hapten) + Enzyme-(avidin/anti-hapten detection probe) + DAB |
| | 1° detection probe + 2° detection probe + 3° detection probe-(biotin/hapten) + Enzyme-(avidin/anti-hapten detection probe) + Chromogen |
| | 1° detection probe + 2° detection probe + 3° detection probe-(biotin/hapten) + Enzyme-(avidin/anti-hapten detection probe) + QM-Dye |
| | 1° detection probe + 2° detection probe + 3° detection probe-(biotin/hapten) + Enzyme-(avidin/anti-hapten detection probe) + Tyramide-Dye |

In a specific embodiment, the detection probes set forth in Table 2 are antibodies.

Non-limiting examples of commercially available detection reagents or kits comprising detection reagents suitable for use with present methods include: VENTANA ultraView detection systems (secondary antibodies conjugated to enzymes, including HRP and AP), VENTANA iVIEW detection systems (biotinylated anti-species secondary antibodies and streptavidin-conjugated enzymes); VENTANA OptiView detection systems (OptiView) (anti-species secondary antibody conjugated to a hapten and an anti-hapten tertiary antibody conjugated to an enzyme multimer); VENTANA Amplification kit (unconjugated secondary antibodies, which can be used with any of the foregoing VENTANA detection systems to amplify the number of enzymes deposited at the site of primary antibody binding); VENTANA OptiView Amplification system (Anti-species secondary antibody conjugated to a hapten, an anti-hapten tertiary antibody conjugated to an enzyme multimer, and a tyramide conjugated to the same hapten. In use, the secondary antibody is contacted with the sample to effect binding to the primary antibody. Then the sample is incubated with the anti-hapten antibody to effect association of the enzyme to the secondary antibody. The sample is then incubated with the tyramide to effect deposition of additional hapten molecules. The sample is then incubated again with the anti-hapten antibody to effect deposition of additional enzyme molecules. The sample is then incubated with the detectable moiety to effect dye deposition); VENTANA DISCOVERY, DISCOVERY OmniMap, DISCOVERY UltraMap anti-hapten antibody, secondary antibody, chromogen, fluorophore, and dye kits, each of which are available from Ventana Medical Systems, Inc. (Tucson, Ariz.); PowerVision and PowerVision+ IHC Detection Systems (secondary antibodies directly polymerized with HRP or AP into compact polymers bearing a high ratio of enzymes to antibodies); and DAKCO EnVision™+ System (enzyme labeled polymer that is conjugated to secondary antibodies).

Figure 4A:
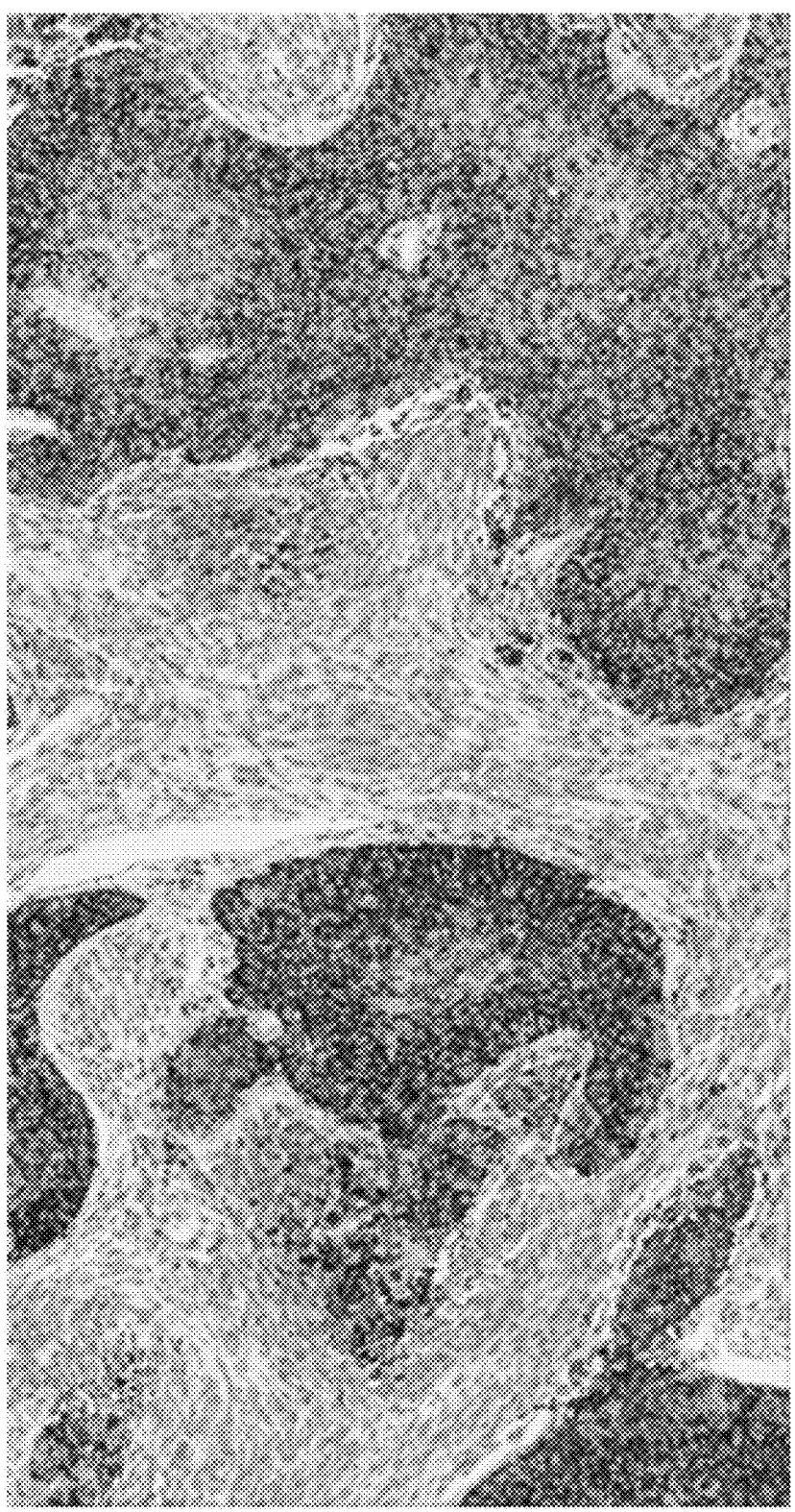
FIG. 4A provides an example of a tissue specimen where PD-L1 positive tumor cells are stained with DAB (brown), tumor infiltrating lymphocytes are stained with DISCOVERY Purple (fuchsia), where those lymphocytes that co-express PD-L1 appear are spotted with purple and brown.
Figure 5A:
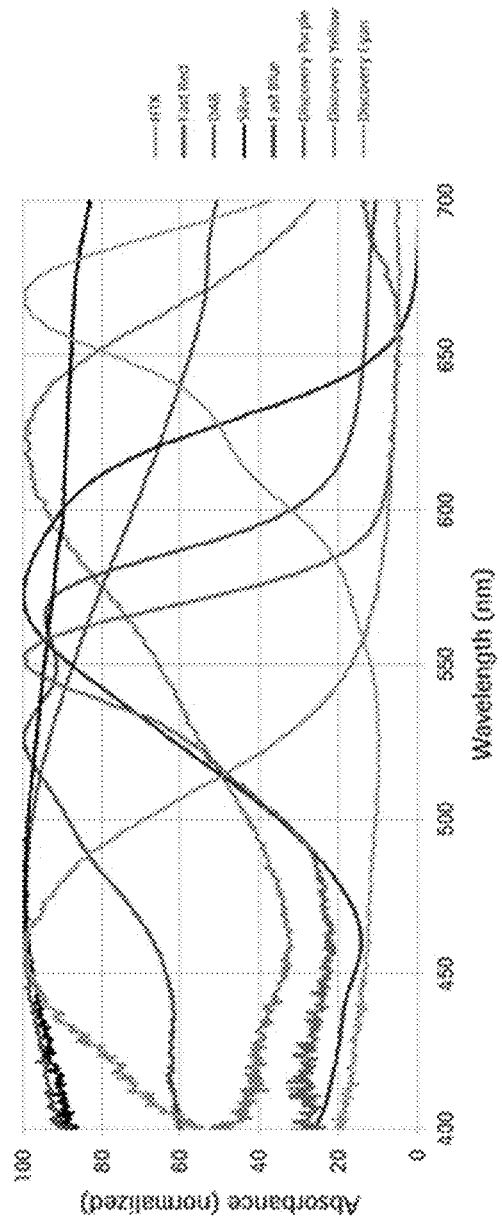
FIG. 5A provides a graph illustrating the absorption spectra of several chromogens.
Figure 5B:
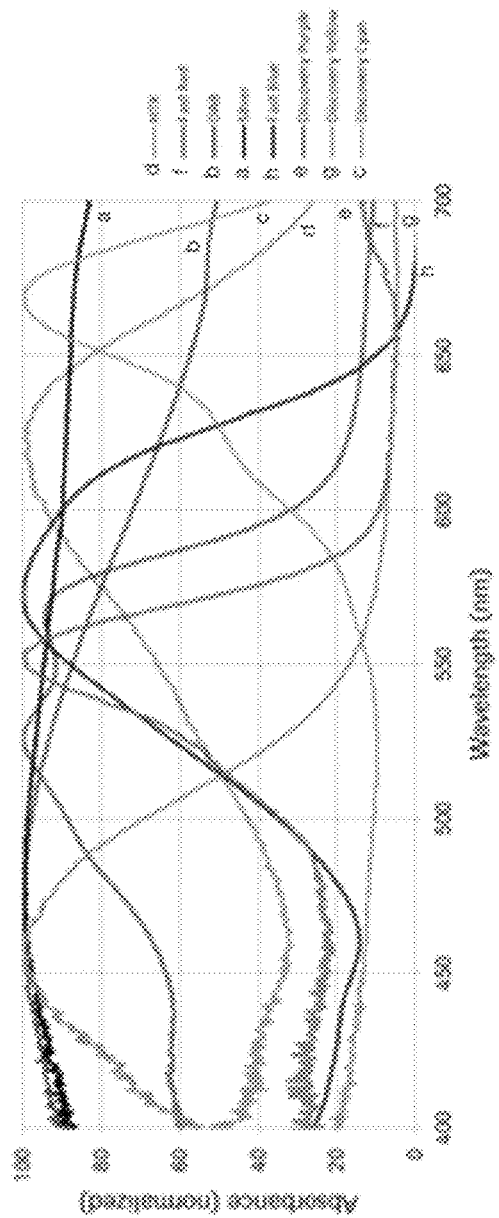
FIG. 5B provides a graph illustrating the absorption spectra of several chromogens.

In yet further embodiments, the detection reagents are selected such that the detectable moieties, when introduced to the tissue specimen, provide for different colors (e.g. yellow, blue, fuchsia). In some embodiments, the detectable moieties are selected such that they provide a good contrast between each other, i.e. a separation of colors that are optically recognizable and/or which help to facilitate detection (manually or via automated methods) of the differently stained targets (e.g. brown and purple). For example, FIG. 5 provides a graph illustrating the absorbance spectra of several chromogens. As illustrated, DISCOVERY Purple is believed to be superior to the other chromogens enumerated in FIG. 5 when used in conjunction with DAB in a multiplex assay, due to the narrow absorbance peak of DISCOVERY Purple as compared with absorbance peaks of the other chromogens. As shown in FIGS. 4A through 4C, such a color combination provides good contrast and a clear identification of PD-L1 positive immune cells, and allows PD-L1 positive immune cells to be differentiated from PD-L1 positive tumor cells.

In other embodiments, the substrates or signaling conjugates are selected such that peak detectable wavelengths of any detectable moiety do not overlap with each other and are readily detectable by a pathologist or an optical detector (e.g. a scanner). In some embodiments, the detectable moieties are selected such that the peak wavelengths of the different detectable moieties are separated by at least about 50 nm. In other embodiments, the detectable moieties are selected such that the peak wavelengths of the different detectable moieties are separated by at least about 70 nm. In yet other embodiments, the detectable moieties are selected such that the peak wavelengths of the different detectable moieties are separated by at least about 100 nm.

In some embodiments, the ordering of application of the substrates in any multiplex assay is important. For example, a particular substrate may not be as sensitive when used to detect one particular target as compared with another. Moreover, it is believed that proper ordering may prevent masking of signals in close proximity to each other. In some embodiments, the first detection reagent to be applied is specific to PD-L1 and the second detection reagent to be applied is specific to the at least one immune cell marker.

Methods of Multiplex Detection

In some embodiments, the present disclosure provides methods for the multiplex detection of targets (e.g. PD-L1 positive tumor cells and immune cells) within a tissue sample. While certain non-limiting embodiments and examples described herein may provide for the indirect detection of primary antibodies utilizing brightfield microscopy, the person of ordinary skill in the art will appreciate that the detection probes used herein are not limited to primary antibodies and any detection probes utilized may detected directly or indirectly, and detection may be facilitated with chromogens, fluorophores, quantum dots, etc. as. known to those of ordinary skill in the art.

Compared with prior art methods, the multiplex assays and methods of the present disclosure allow for improved detection accuracy of PD-L1 positive immune cells and a more efficient workflow. In fact, the. presently disclosed multiplex assays and methods allow for the identification of PD-L1 positive immune cells on a single slide of a tissue sample and without the need to swap between slides stained with a primary stain (e.g. hematoxylin and eosin stain ("H&E")) and slides stained in an IHC assay for the PD-L1 biomarker. In contrast to the methods disclosed herein, the prior art methods utilized a single detection probe to stain both PD-L1 positive tumor cells and PD-L1 positive immune cells and analysis and scoring of the stained tissue sample required a pathologist to alternate between those slides stained with a primary stain and those stained by IHC. For example, according to prior art methods, a pathologist would first identify tumor tissue in an H&E stained slide, then switch to an IHC stained slide to identify PD-L1 positive tumor cells. Subsequently, the pathologist would switch back to the H&E stained slide to identify immune cells within the positive area, followed by again switching back to the IHC stained slide to assess immune cell PD-L1 positivity. The disclosed methods, on the other hand, require only two steps, namely identifying a tumor with a primary H&E stain, followed by identification of positive staining tumor cell and immune cells that co-express PD-L1 and at least one immune cell marker on a single slide. It is through the incorporation of a secondary biomarker that Applicants have achieved the superior results.

In some embodiments, the method of multiplex detection comprises contacting the tissue sample with at least two different detection probes (e.g. primary antibodies) such that (i) PD-L1 positive tumor cells, and (ii) immune cells may be detected (e.g. those immune cells that are PD-L1 positive and those immune ceils that are PD-L1 negative). In some embodiments, application of the detection probes to a tissue sample allows PD-L1 positive tumor cells to be differentiated from PD-L1 positive immune cells (especially those PD-L1 positive immune cells that are infiltrating PD-L1 positive tumor tissue). In other embodiments, introduction of the detection probes to a tissue sample allows PD-L1 positive tumor cells, PD-L1 positive immune cells, PD-L1 negative tumor cells, and/or PD-L1 negative immune cells to be identified and/or quantitated. In other embodiments, the application of the detection probes and detection reagents to a tissue sample enables PD-L1 positive tumor cells to be identified with a first color (a first chromogen), immune cells to be identified with a second color (a second chromogen), and PD-L1 positive immune cells to be identified as co-expressing the first and second colors (the first and second chromogens). For example, as shown in FIG. 4, PD-L1 tumor cells are identified with a brown color (DAB), immune cells are identified with a fuchsia color (DISCOVERY Purple), and those immune cells that are PD-L1 positive, i.e. those immune cells which co-express PD-L1 and an immune cell marker, comprise or co-express both the brown color and fuchsia color.

In some embodiments, the multiplex assays and methods of the present disclosure comprise introducing a detection probe specific for PD-L1 and at least one detection probe specific tor at least one immune cell marker. In some embodiments, the at least one detection probe specific for at least one immune cell marker is a primary antibody. In the context of primary antibodies for detecting the at least one immune cell marker, the skilled artisan will recognize that multiple primary antibodies may be utilized, where each primary antibody is specific to a different immune cell marker. For example, an anti-CD4 antibody may be introduced (simultaneously or sequentially) along with an anti-CD8 antibody, where each of the anti-CD4 and anti-CD8 antibodies may be detected indirectly with the same or different chromogens (or other detection reagents). In other embodiments, an anti-CD45LCA antibody may be introduced (simultaneously or sequentially) along with a primary antibody selected from the group consisting of an anti-CD3 antibody, an anti-CD4 antibody, and an anti-CD8 antibody where again, each of the antibodies specific to the immune cells markers may be detected with the same or different chromogens (or other detection reagents). In other embodiments, only a single detection probe specific to at least one immune cell marker is utilized (e.g. an anti-CD45LCA primary antibody).

Figure 6:
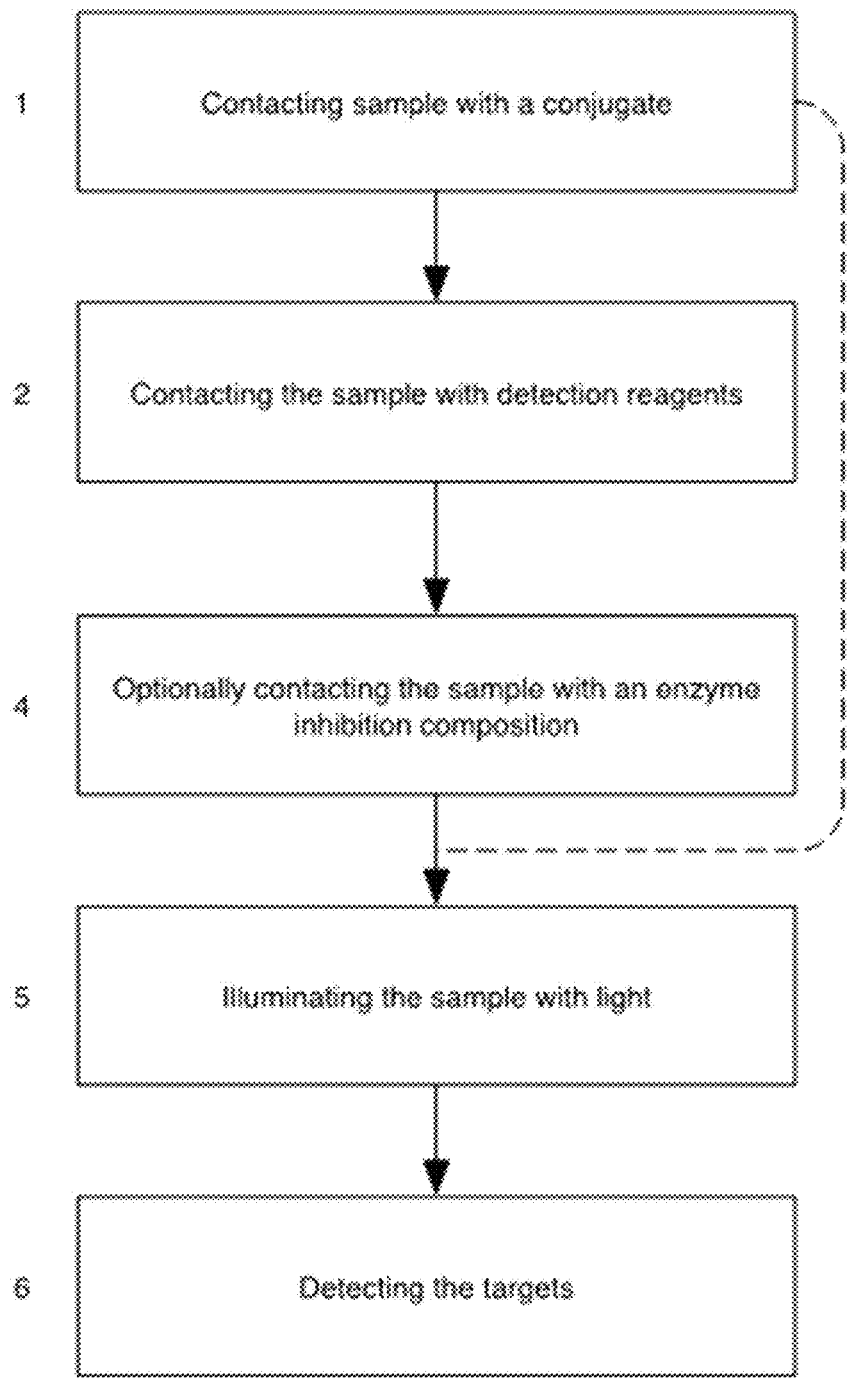
FIG. 6 is an exemplary flowchart illustrating methods for performing a multiplex assay according to non-limiting embodiments of the present disclosure.
Figure 7:
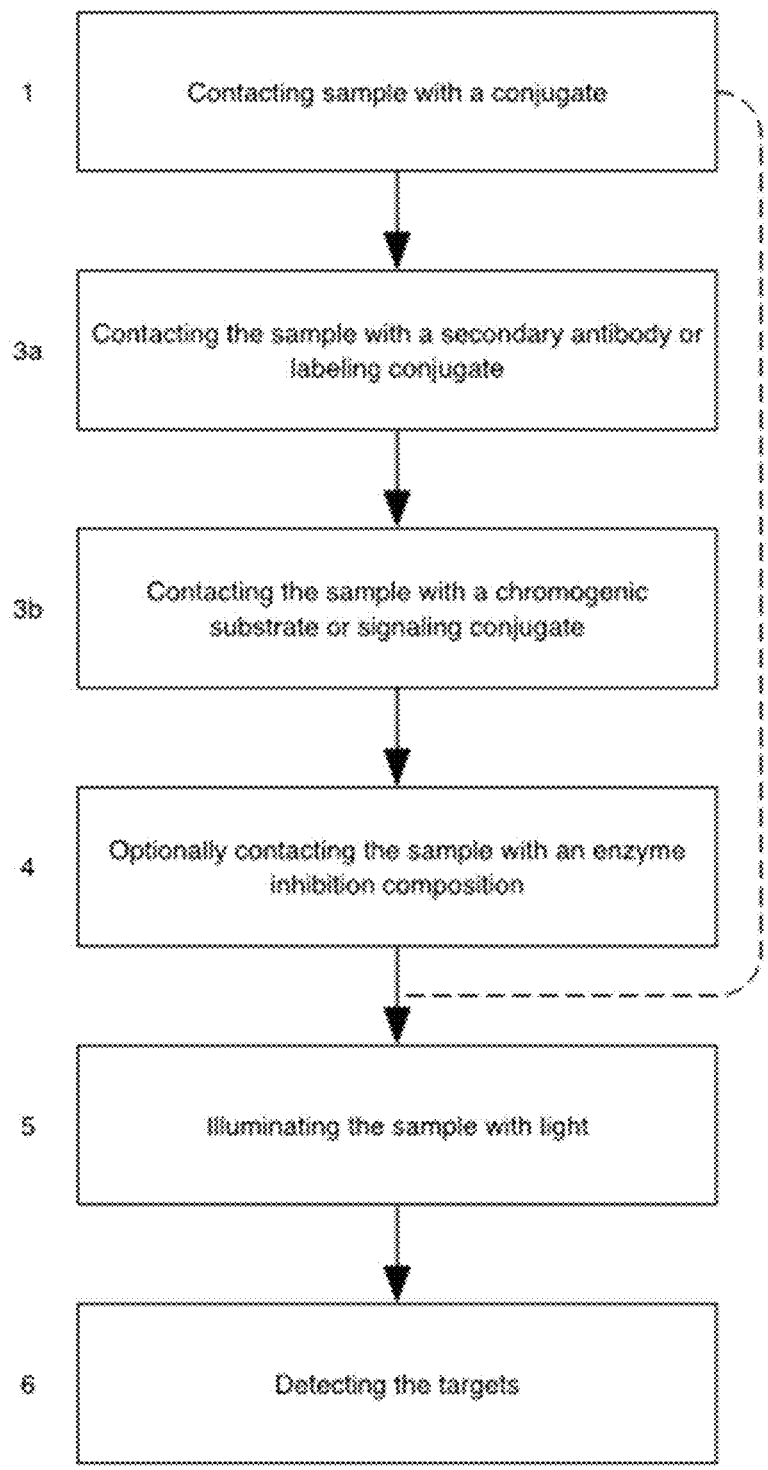
FIG. 7 is an exemplary flowchart illustrating methods for performing a multiplex assay according to non-limiting embodiments of the present disclosure.

FIGS. 6 and 7 provide flowcharts delineating the steps of certain embodiments of the methods of the present disclosure. In particular, the method sets forth a multiplex detection scheme where at step 1 the sample is contacted with a detection probe (e.g. a primary antibody specific for PD-L1). When the detection probe is introduced into the sample, it will form a detection probe-target complex (e.g. a primary antibody-target complex). A subsequent step 2 includes contacting the sample with detection reagents. The detection reagents may include (i) labeling conjugates and, (ii) chromogenic substrates or signaling conjugates, as illustrated in steps 3a and 3b of FIG. 7. A further subsequent step 4 comprises contacting the sample with an enzyme inhibition composition (or, a step where an enzyme and/or antibody stack comprising the detection reagents is inhibited or denatured). A dashed line indicates that the process of steps 1 through 4 may be repeated one or more times to provide for the sequential multiplex detection of multiple, different targets within the tissue sample (e.g. immune cells marks; other tumor markers). The method also comprises a step 5 of illuminating sample with light and detecting the targets at step 6. Detection may be manual or automated and may optionally be tied to a computer system and/or an imaging system.

As an alternative to the embodiments provided in FIGS. 6 and 7, each of the different detection probes may be added simultaneously or sequentially, and before any detection reagent is added. For example, a first detection probe may be added followed by introduction of a second detection probe (and, of course, "n" additional detection probes, if called for by the assay). Subsequently, first detection reagents may be added, followed by denaturing, inhibiting, and/or eluting any enzyme and/or associated antibodies included with the first detection reagents. Following that step, second detection reagents and any additional "n" number of direction reagents may be added, based on the "n" number of detection probes provided. At that point, the first and second detection reagents may be detected simultaneous.

As a further example of a multiplex assay according to the present disclosure, a first primary antibody specific to a first target (e.g. specific to one of PD-L1 or an immune cell marker) is introduced to a tissue sample. In some embodiments, the first primary antibody forms a detectable first target-antibody conjugate complex. Either simultaneously or subsequently, a second primary antibody specific to a second target (e.g. the other PD-L1 or the immune cell marker) comprising a second label is introduced to the sample to form a second target-antibody conjugate. Third, fourth, and nth additional detection probes specific to other targets (forming "n" target-detection probe complexes) may be further introduced, again either sequentially or simultaneously with the first and/or second primary antibodies. After the detection probes are deposited, they may be detected, either directly or indirectly depending, of course, on their configuration. In some embodiments, additional detection reagents are introduced to enable the detection of the targets and the additional detection reagents include those described herein. In some embodiments, fist, second, and nth detection reagents are introduced, where each of the first, second, and nth detection reagents comprise (i) a secondary antibody specific to each of the detection probes, wherein the secondary antibody is conjugated to an enzyme; and (ii) a chromogenic substrate; wherein each of the first, second, and nth chromogenic substrates are different.

In some embodiments, the multiplex detection method comprises the steps of (i) contacting a biological sample with a first detection probe (e.g. one of a primary antibody specific for PD-L1 or CD45LCA) to form a first antibody-target complex; (ii) contacting the biological sample with a first labeling conjugate wherein the first labeling conjugate comprises a first enzyme (where the first labeling conjugate is an anti-species antibody that specifically binds to the first detection probe and is configured to label the target with an enzyme); (iii) contacting the biological sample with a first signaling conjugate comprising a first latent reactive moiety and a first detectable moiety; (iv) inactivating the first enzyme, such as by contacting the sample with a first enzyme inactivation composition to substantially inactivate or completely inactivate the first enzyme contained in the biological sample. In some embodiments, the first detection probe added is a primary antibody specific for PD-L1, e.g. an anti-PD-L1 antibody. In some embodiments, the first signaling conjugate comprises a dye linked to a chemical moiety that, when reacted with an appropriate enzyme and under suitable conditions, deposits a dye selected from the group consisting of DISCOVERY Purple, Cy5, Rhodamine and DABSYL. In other embodiments, the first signaling conjugate includes DAB as a substrate.

After the first enzyme is inactivated (optional), the multiplex method further comprises the steps of (v) contacting a biological sample with a second detection probe (e.g. the other of the primary antibody specific for PD-L1 or CD45LCA) to form a second antibody-target complex; (vi) contacting the biological sample with a second labeling conjugate wherein the second labeling conjugate comprises a second enzyme (where the second labeling conjugate is an anti-species antibody that specifically binds to the second detection probe and is configured to label the target with an enzyme); (vii) contacting the biological sample with a second signaling conjugate comprising a second latent reactive moiety and a second detectable moiety; (viii) inactivating the second second enzyme, such as by contacting the sample with a first enzyme inactivation composition to substantially inactivate or completely inactivate the first enzyme contained in the biological sample. In some embodiments, the second detection probe added is a primary antibody specific for a tumor cell marker, e.g. an anti-CD45LC antibody. In some embodiments, the second signaling conjugate comprises a detectable moiety selected from the group consisting of DAB, DISCOVERY Purple, Cy5, Rhodamine and DABSYL, where the second detectable moiety is different than the first detectable moiety. In other embodiments, the second signaling conjugate includes QM-DISCOVERY Purple as a substrate.

After the second enzyme is inactivated, the method may be repeated such that additional detection probes (e.g. primary antibodies or nucleic acid probes) may be introduced, along with additional detection reagents, to effectuate detection of other targets (e.g. other immune cells receptors, EGFR, HER2, HER2/neu, HPV, ALK, etc.). In some embodiments, a third detection probe is introduced to detect a tumor marker other than PD-L1. Following introduction of all of the primary antibodies (and other detection probes) and respective detection reagents or kits, the method further comprises the step of detecting signals (manually or via an automated method) from the first, second, and nth detectable moieties, wherein each of the first, second, and nth detectable moieties are each different. Alternatively, and as noted herein, each of the detection probes may be added simultaneously or sequentially, but before any labeling conjugate is added. As another example, three detection probes may be sequentially applied at step 1, prior to introduction of any detection reagents.

In the context of a multiplex assay where multiple reagents are detected sequentially, it is desirable to substantially inactivate (e.g. greater than 90% inactivation) any reagent or endogenous enzymes between successive detection steps. As a result, it is believed that enzymes present in any one detection step will not interfere with those in a later detections step. This in turn is believed to improve upon the visualization and detection of the different chromogens used in the multiplex assay. Any enzyme inactivation composition known in the art may be used for this purpose. In some embodiments, an-enzyme inactivation composition is applied to inactivate the reagent or endogenous enzymes after each detection step. Exemplary enzyme inactivation compositions and methods are disclosed in co-pending application U.S. 62/159,297, the disclosure of which is incorporated by reference herein in its entirety.

In some embodiments, a denaturation step prevents the enzyme used in a first set of detection reagents from acting on a second substrate. In some embodiments, the denaturant is a substance that denatures the enzyme in the first detection reagent set. In some embodiments, the denaturant is, for example, formamide, an alkyl-substituted amide, urea or a urea-based denaturant, thiourea, guanidine hydrochloride, or derivatives thereof. Examples of alkyl-substituted amides include, but are not limited to, N-propylformamide, N-butyl-formamide, N-isobutylformamide, and N,N-dipropylafor-mamide. In some embodiments, the denaturant is provided in a buffer. In some embodiments, the sample is treated with the denaturant for a period of time and under conditions sufficient to denature the first target probe detection enzyme, for example alkaline phosphatase. In some embodiments, the sample is treated with the denaturant for about 15 to about 30 minutes, preferably about 20 to 24 minutes at about 37° C. In some embodiments, the sample is treated with the denaturant for a period of time and under conditions sufficient to denature the target enzyme while preserving hybridization of the second nucleic acid probe to the target.

Conditions suitable for introducing the signaling conjugates or substrates with the biological sample are used, and typically include providing a reaction buffer or solution that comprises a peroxide (e.g., hydrogen peroxide), and that has a salt concentration and pH suitable for allowing or facilitating the enzyme to perform its desired function. In general, this step of the method is performed at temperatures ranging from about 35° C. to about 40° C., although the skilled artisan will be able to select appropriate temperature ranges appropriate for the enzymes and signalizing conjugates selected. For example, it is believed that these conditions allow the enzyme and peroxide to react and promote radical formation on the latent reactive moiety of the signaling conjugate. The latent reactive moiety, and therefore the signaling conjugate as a whole, will deposit covalently on the biological sample, particularly at one or more tyrosine residues proximal to the immobilized enzyme conjugate, tyrosine residues of the enzyme portion of the enzyme conjugate, and/or tyrosine residues of the antibody portion of the enzyme conjugate. The biological sample is then illuminated with light and the target may be detected through absorbance of the light produced by the detectable moiety of the signaling conjugate.

The multiplex assays, methods, and systems may be either fully manual, or may include automated steps. In some embodiments, an automated method may be implemented on an automated IHC/ISH slide stainer. Automated IHC/ISH slide stainers typically include at least a stainer unit for dispensing reagent to implement staining protocols onto a slide. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER Link 48 (Agilent Technologies) and intelliPATH (Biocare Medical) stainers); (2) liquid overlay technology, in which reagents are either covered with or dispensed through an inert fluid layer deposited over the sample (such as implemented on VENTANA BenchMark and DISCOVERY stainers); (3) capillary gap staining, in which the slide surface is placed in proximity parallel to another surface (which may be another slide or a coverplate) to create a narrow gap, through which capillary forces draw up and keep liquid reagents in contact with the samples (such as the staining principles used by DAKO TECH-MATE, Leica BOND, and DAKO OMNIS stainers). Some iterations of capillary gap staining do not mix the fluids in the gap (such as on the DAKO TECHMATE and the Leica BOND). In other variations of capillary gap staining, the reagents are mixed in the gap, such as in translating gap technology, in which a gap is created between the slide and a curved surface and movement of the surfaces relative to one another effects mixing (see U.S. Pat. No. 7,820,381); and dynamic gap staining, which uses capillary forces similar to capillary gap staining to apply sample to the slide, and then translates the parallel surfaces relative to one another to agitate the reagents during incubation to effect reagent mixing (such as the staining principles implemented on DAKO OMNIS slide stainers (Agilent)). It has recently been proposed to use inkjet technology to deposit reagents on slides. See WO 2016-170008 A1. This list of staining principles is not intended to be exhaustive, and the present methods and systems are intended to include any staining technology (both known, and to be developed in the future) that can be used to apply the appropriate reagents to the sample.

If the specimen is a sample embedded in paraffin, the sample can be deparaffinized manually or with the automated IHC/ISH slide stainer using appropriate deparaffinizing fluid(s). After the waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The automated IHC/ISH slide stainer can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label or reporter molecule. Labels can include radioactive isotopes, enzyme substrates, co-factors, ligands, chemiluminescent or fluorescent agents, haptens, and enzymes.

Specific examples of automated IHC/ISH slide stainer, including the itelliPATH (Biocare Medical), WAVE (Celerus Diagnostics), DAKO OMNIS and DAKO AUTOSTAINER LINK 48 (Agilent Technologies), BENCHMARK (Ventana Medical Systems, Inc.), Leica BOND, and Lab Vision Autostainer (Thermo Scientific) automated slide stainers are described by Prichard, *Overview of Automated Immunohistochemistry*, Arch Pathol Lab Med., Vol. 138, pp. 1578-1582 (2014), incorporated herein by reference in its entirety. Additionally, Ventana Medical Systems, Inc. is the assignee of a number of U.S. patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Alternatively, specimens can be manually processed.

After the specimens are stained (either manually or on an automated slide stainer), the stained slides can be imaged on a brightfield imager slide scanner. At a basic level, slide scanners generate a representative digital image of the stained sample. The typical brightfield slide scanner includes at least: (1) a microscope with lens objectives, (2) a light source (such as halogen, light emitting diode, white light, and/or multispectral light sources), (3) robotics to move glass slides around (or to move the optics around the slide), (4) one or more digital cameras for image capture, (5) a computer and associated software to control the robotics and to manipulate, manage, and view digital slides. Digital data at a number of different X-Y locations (and in some cases, at multiple Z planes) on the slide are captured by the-camera's charge-coupled device (CCD), and the images are joined together to form a composite image of the entire scanned surface. Common methods to accomplish include:

(1) Tile based scanning, in which the slide stage or the optics are moved in very small increments to capture square image frames, which overlap adjacent squares to a slight degree. The captured squares are then automatically matched to one another to build the composite image; and (2) Line-based scanning, in which the slide stage moves in a single axis during acquisition to capture a number of composite image "strips." The image strips can then be matched with one another to form the larger composite image. In some cases, A detailed overview of various brightfleld scanners can be found at Farahani et al., *Whole slide imaging in pathology: advantages, limitations, and emerging perspectives*, Pathology and Laboratory Medicine Int'l, Vol. 7, p. 23-33 (June 2015), the content of which is incorporated by reference in its entirety. Examples of slide scanners include: 3DHistech PANNORAMIC SCAN II; DigiPath PATHSCOPE; Hamamatsu NANOZOOMER RS, HT, and XR; Huron TISSUESCOPE 4000, 4000XT, and HS; Leica SCAN SCOPE AT, AT2, CS, FL, and SCN400; Mikroscan D2; Olympus VS120-SL; Omnyx VL4, and VL120; PerkinElmer LAMINA; Philips ULTRA-FAST SCANNER; Sakura Finetek VISIONTEK; Unic PRECICE 500, and PRECICE 600x; VENTANA ISCAN COREO and ISCAN HT; and Zeiss AXIO SCAN.Z1. Other exemplary systems and features can be found in, for example, International Patent Application No.: PCT/US2010/002772 (Patent Publication No.: WO/2011/049608) entitled IMAGING SYSTEM AND TECHNIQUES or disclosed in U.S. Patent Application No. 61/533,114, filed on Sep. 9, 2011, entitled IMAGING SYSTEMS, CASSETTES, AND METHODS OF USING THE SAME. International Patent Application No. PCT/US2010/002772 and U.S. Patent Application No. 61/533,114 are incorporated by reference in their entities.

The digital images generated by slide scanners may be further analyzed using various digital pathology software suites. These computer programs typically operate by measuring the signal intensity of signal channel at each pixel of the digital image. Various algorithms can then be applied to the signal data generated therefrom to, for example, identify object, calculate various statistics about signals correlating to the various dyes, including mean signal intensity, area of staining across the entire image or at specific regions of interest, etc. Additionally, these software packages often have, functionality that allow the user to manipulate the image, including to zoom in and out, to identify various regions of interest, annotate objects and/or regions, etc. Examples of these software packages, include VENTANA VIRTUOSO (Roche); Definiens TISSUE STUDIO, DEVELOPER XD, and IMAGE MINER; and Visopharm BIOTOPIX, ONCOTOPIX, and STEREOTOPIX software packages.

Detection Kits

Also disclosed are systems and kits comprising (i) a detection probe specific to PD-L1, and (ii) at least one detection probe specific to at least one immune cell marker. In some embodiments, the kits are used to co-stain immune cells that express PD-L1 and an immune cell marker. In some embodiments, the kits are used to stain tissue samples such that PD-L1 positive tumor cells, PD-L1 immune cells, PD-L1 negative tumor cells, and PD-L1 negative immune cells may be identified and/or differentiated from each other. In some embodiments, the kits allow for tumor infiltrating PD-L1 positive immune cells to be detected and/or quantified, where the results of detection and/or quantification of the tumor infiltrating PD-L1 positive tumor cells may be used alone or in conjugation with other data (e.g. results of scoring tissue samples) to predict the response to PD-L1 targeted therapies. In some embodiments, the results of tissue staining with the disclosed kits may be used by medical professionals to determine a course of treatment (e.g. anti-PD-L1 therapy or co-therapy with an anti-PD-L1 agent), such as treatment for cancer where the cancer comprise tumors cells which express or overexpress PD-L1.

In some embodiments, the detection probes used in the kits are primary antibodies. In other embodiments, the detection probes used in the kits are nucleic acid probes. In other embodiments, the detection probes used in the kits comprise a combination of primary antibodies and nucleic acid probes. In some embodiments, the detection probe specific to PD-L1 is a primary antibody, e.g. an anti-PD-L1 antibody. In some embodiments, the detection probe specific to at least one immune cell marker is a primary antibody specific to at least one of CD3, CD4, CD8, CD45, and CD45LCA. In some embodiments, the first primary antibody is an anti-PD-L1 antibody (SP142). In some embodiments, the second primary antibody is an anti-CD45LCA antibody (RP2/18).

In some embodiments, the kit further comprises one or more detection reagents or detection kits. In some embodiments, the kit further comprises a first labeling conjugate specific to the first primary, antibody; and a second labeling conjugate specific to the second primary antibody. In some embodiments, the kit further comprises first and second substrates or first and second signaling conjugates, wherein the first and second substrates or signaling conjugates are different. The labeling conjugates, signaling conjugates, chromogenic substrates, and/or chromogens may include any of those enumerated herein or otherwise known to those of skill in the art. In some embodiments, the kit further comprises one or more enzyme inactivation compositions specific to the enzymes of the labeling conjugates.

In some embodiments, the kits include instructions for the multiplex detection of markers or instructions for predicting the outcome of therapy based on the presence of PD-L1 positive tumor infiltrating lymphocytes. In other embodiments, the kits include instructions for the administration of appropriate active pharmaceutical ingredients based on the whether tumor infiltrating PD-L1 positive lymphocytes are detected in a region of a tissue sample comprising PD-L1 positive tumor tissue. In some embodiments, the kits include one or more therapeutic agents. The kits may further comprise instructions or protocols for scoring and/or instructions or protocols for determining a staging or a grade of a particular cancer based on the presence and/or quantity of PD-L1 positive tumor cells, PD-L1 positive immune cells (including those PD-L1 positive lymphocytes that are infiltrating PD-L1 positive tumor tissue).

The kits may include other reagents, e.g. buffers, primary stains, blocking agents, microscope coverslips, etc.

In some embodiments, the kits may comprise at least one other detection probe specific for EGFR, HER2, HPV, ALK, BRAF, OX-40, PD-1, IDO-1, FoxP3, CD163, and CTLA-4.

Scoring of Tissue Samples

In another aspect of the present disclosure is a method of scoring a tumor sample for PD-L1 expression, the method comprising identifying tumor cells and immune cells in the tissue sample (such as by utilizing the multiplex methods and kits described herein); determining a number of tumor cells expressing PD-L1 and a number immune cells expressing PD-L1 and/or the relative intensity of PD-L1 expression in the cells; and categorizing a tumor according to PD-L1 expression. In some embodiments, to score the tumor cells, the fraction of PD-L1-positive tumor cells is divided by the total number of tumor cells (i.e., PD-L1 positive and PD-L1 negative tumor cells). In some embodiments, to score the immune cells, the area in the image that contains, these cells is measured and a fraction of the tumor area that contains PD-L1-positive lymphocytes (immune cells) is scored. In some embodiments, the expression of PD-L1 is determined by specifically detecting PD-L1 protein and/or PD-L1 mRNA in the tumor. In some embodiments, the cells are considered to express PD-L1 when the cell has at least partial membrane staining of PD-L1 protein detected by IHC. In some embodiments, the tumor is categorized according to one or both of a modified H-score (MHS) or a modified proportion score (MPS), as those procedures are known to those of ordinary skill in the art.

In yet another aspect of the present disclosure is a method of scoring PD-L1 expression in tumor tissue sections that have been stained with an anti-PD-L1 antibody and stained for the presence of at least one immune cell marker. In some embodiments, the results of scoring processes may be used to select patients for treatment with anti-PD-L1 therapies, e.g., as enrollment criteria in a clinical trial, to predict response of a subject to anti-PD-L1 therapies, and in methods of treating a patient for cancer.

In other embodiments, the samples are scored according to the following:

Tumor infiltrating immune cells may be scored as the percentage of PD-L1 positive immune cells showing any discernible PD-L1 (SP142) staining of any intensity in the total tumor area (See Table 3). Tumor area is defined as the area occupied by the tumor cells and the associated intratumoral and contiguous peri-tumoral stroma that includes lymphocytes, macrophages, and cells with dendritic or reticular morphology.

TABLE 3

Scoring Algorithm for the VENTANA PD-L1 (SP142) assay in NSCLC tissue (IC 5% Cut-Off)

| Microscopic Observation | PD-L1 (SP142) Status |
|---|---|
| Absence of any discernible PD-L1 staining. OR Presence of discernible PD-L1 staining of any intensity in tumor infiltrating immune cells covering ≤5% of tumor area occupied by tumor cells, associated intratumoral, and contiguous peritumoral stroma | Negative |
| Presence of discernible PD-L1 staining of any intensity in tumor infiltrating immune cells covering ≥5% of tumor area occupied by tumor cells, associated intratumoral; and contiguous peritumoral stroma | Positive. |

Stain intensity of immune cells (IC): The intensity of PD-L1 (SP142) staining of tumor infiltrating immune cells is recorded on score sheets (usually for informational purposes) using the criteria described in Table 4.

TABLE 4

Intensity Assessment of Tumor Infiltrating Immune Cells: VENTANA PD-L1 (SP142) assay in NSCLC Tissue

| Stain Intensity Score* | Stain Intensity Description for Immune Cells |
|---|---|
| 0 | NEGATIVE staining of tumor infiltrating immune tells covering the tumor area occupied by tumor cells, associated intratumoral, and contiguous peri-tumoral desmoplastic stroma |
| 1+ | WEAK membrane staining of tumor infiltrating immune cells covering the tumor area occupied by tumor cells, associated intratumoral, and contiguous peri-tumoral desmoplastic stroma |
| 2+ | MODERATE membrane staining of tumor infiltrating immune cells covering the tumor area occupied by tumor cells, associated intratumoral, and contiguous peri-tumoral stroma |
| 3+ | STRONG membrane staining of tumor cells covering the tumor area occupied by tumor cells, associated intratumoral, and contiguous peri-tumoral stroma |
| Not Evaluable (N/E) | Interpretation is not possible, e.g., no tissue/tumor present, artifacts, or edge artifacts |

Stain intensity of tumor cells (TC): The intensity of PD-L1 (SP142) staining of tumor cells (TC) is recorded on score sheets (for informational purposes) in using the criteria described in Table 5.

TABLE 5

Intensity Assessment of Tumor Cells: VENTANA PD-L1 (SP142) assay in NSCLC Tissue

| Stain Intensity Score | Stain Intensity Description |
| --- | --- |
| 0 | NEGATIVE staining of the tumor cells |
| 1+ | WEAK membrane staining of the tumor cells |
| 2+ | MODERATE membrane staining of the tumor cells |
| 3+ | STRONG membrane staining of the tumor cells |
| Not Evaluable (N/E) | Interpretation is not possible, e.g., no tissue/tumor present, artifacts, or edge artifacts |

Tumors cells are scored as the percentage of viable tumor cells showing any discernible PD-L1 (SP142) membrane staining (Table 6).

TABLE 6

Scoring Algorithm for the VENTANA PD-L1 (SP142) assay in NSCLC tissue (TC 5% Cut-Off)

| Microscopic Observation | PD-L1 (SP142) Status |
| --- | --- |
| Absence of any discernible PD-L1 staining. OR Presence of discernible PD-L1 membrane staining of any intensity in <5% of tumor cells | Negative |
| Presence of discernible PD-L1 membrane staining of any intensity in ≥5% of tumor cells | Positive |

Nonspecific background staining is unexpected staining that diverges from a typical staining pattern. Non-specific staining is evaluated on PD-L1 (SP142) antibody-stained NSCLC test specimen slides according to the criteria in Table 7 and recorded as Acceptable or Unacceptable.

TABLE 7

Background Assessment: VENTANA PD-L1 (SP142) assay in NSCLC and Tonsil Tissue

| | Microscope Observation | Score |
| --- | --- | --- |
| Acceptable | No background staining | 0 |
| | Slight discernible non-specific staining that is not obtrusive to interpretation of specific staining | 0.25 |
| | Some discernible non-specific staining that is not obtrusive to interpretation of specific staining | 0.5 |
| Unacceptable | Some discernible non-specific staining that is slightly obtrusive to interpretation of specific staining | 0.75 |
| | Non-specific staining is obtrusive to interpretation of specific staining | 1 |
| | Non-specific staining is very obtrusive to interpretation of specific staining | 1.5 |
| | Non-specific staining is extremely obtrusive but is not as intense as specific staining | 2 |
| | Non-specific staining intensity is almost equivalent to the intensity of the specific staining | 2.5 |
| | Non-specific staining cannot be differentiated from specific staining | 3 |

Methods of Predicting a Response to Therapy and Methods of Treatment

In some embodiments, the multiplex assays, kits, and methods disclosed herein may be utilized to predict, or assist in predicting, a response to therapy (e.g. an anti-PD-L1 therapy or co-therapy with an anti-PD-L1 agent) or the results of any assay or method disclosed herein may be used to facilitate treatment with an anti-PD-L1 therapy or co-therapy with an anti-PD-L1 agent. Without wishing to be bound by any particular theory, it is believed that the presence of tumor-infiltrating PD-L1 positive immune cells, e.g. tumor infiltrating lymphocytes, within PD-L1 positive tumor tissue is an indication that a patient may respond well to treatment with an anti-PD-L1 therapy or combination therapy/co-therapy including an anti-PD-L1 agent. Again, it is believed that tumor-infiltrating lymphocytes are recruited into the tumor in an attempt to control tumor growth. Therefore, it is believed that some patients may obtain a benefit from anti-PD-L1 therapies according to the expression of TILs in PD-L1 positive tumor tissue.

Accordingly, in some embodiments is a method of predicting a response to a PD-L1 targeted therapy by analyzing a PD-L1 positive tumor tissue sample for the presence or absence of tumor infiltrating PD-L1 positive immune cells comprising identifying immune cells that co-express PD-L1 and at least one CD marker. In some embodiments, the identifying of the tumor infiltrating PD-L1 positive immune cells comprises contacting the tumor tissue sample with a first detection probe specific for PD-L1 (to form a first detection probe-target complex) and contacting the tumor tissue sample with at least a second detection probe specific for at least one CD marker (to form a second detection probe-target complex). In some embodiments, the detection probe specific to PD-L1 is a primary antibody, e.g. an anti-PD-L1 antibody. In some embodiments, the detection probe specific to the at least one CD marker is an antibody selected from the group selected from an anti-CD3 antibody, an anti-CD4 antibody, an anti-CD8 antibody, and an CD45LCA antibody. In some embodiments, detection reagents are introduced which allow identification of the immune cells which co-express the PD-L1 marker and the at least one CD marker. In some embodiments, the immune cells which co-express PD-L1 marker and the at least one immune cell marker are co-stained with DISCOVERY Purple and DAB. In some embodiments, the PD-L1 targeted therapy is selected from the group consisting of Atezolizumab, Nivolumab, Pembrolizumab, and Pidilizumab and any combination thereof. In some embodiments, the method further comprises introducing at least one other detection probe specific for EGFR, HER2, HPV, ALK, BRAF, OX-40, PD-1, IDO-1, FoxP3, CD163, and CTLA-4.

In addition, in some embodiments is a method of treating cancer in a patient comprising requesting a test providing the results of an analysis to determine whether a PD-L1 positive tumor tissue sample from the patient comprises tumor infiltrating PD-L1 positive lymphocytes and administering a PD-L1 targeted therapy to the patient if the patient's tumor tissue sample expresses PD-L1 positive tumor cells and tumor infiltrating PD-L1 positive lymphocytes. In some embodiments, the test comprises a multiplex assay wherein the tumor tissue sample is contacted with a first primary antibody specific for PD-L1 (e.g. SP142) and a second primary antibody specific for at least one immune cell marker (e.g. RP2/18), wherein the tumor infiltrating PD-L1 positive lymphocytes co-express PD-L1 and the at least one immune cell marker. In some embodiments, detection reagents are introduced which allow identification of the immune cells which co-express the PD-L1 marker and the at least one immune cell marker. In some embodiments, the immune cells which co-express PD-L1 marker and the at least one immune cell marker are co-stained with DISCOVERY Purple and DAB. In some embodiments, the PD-L1 targeted therapy is selected from the group consisting of Atezolizumab, Nivolumab, Pembrolizumab, and Pidilizumab, and any combination thereof. In other embodiments, a PD-L1 targeted therapy is combined with a T-cell stimulating therapy or active pharmaceutical ingredient (including a biological agent). In some embodiments, the method further comprises introducing at least one other detection probe specific for EGFR, HER2, HPV, ALK, BRAF, OX-40, PD-1, IDO-1, FoxP3, CD163, and CTLA-4.

In some embodiments, the PD-L1 expression level in a tumor tissue sample from an individual/patient is compared to a pre-determined cut-off value (e.g. a control value), and this process of detection and comparison may be automated (and, of course, may include a specimen analyzer and a computer system). In some embodiments, a value above the cut-off is considered to represent overexpression of PD-L1 and a value at or below the cut-off is considered as decreased expression of PD-L1. In some embodiments, overexpression for PD-L1 is acknowledged if the expression level for PD-L1 is above a cut-off value between the 50th percentile and the 75th percentile, as established in a control group. In other embodiments, overexpression for PD-L1 is acknowledged if the expression level for PD-L1 is above a cut-off value between the 50th percentile and the 70th percentile, of the control group. In yet other embodiments, individuals/patients are determined as being in need of a PD-L1 therapy or combination therapy including an anti-PD-L1 agent, if PD-L1 is overexpressed (i.e. the PD-L1 expression level determined is above the PD-L1 cut-off value). In some embodiments, if a quantity of PD-L1 positive immune cells exceeds a certain pre-determined cutoff value, then a patient may benefit from treatment with a PD-L1 targeted therapy.

In some embodiments, the methods comprise introducing at least one other detection probe specific for EGFR, HER2, HPV, ALK, BRAF, OX-40, PD-1, IDO-1, FoxP3, CD163, and CTLA-4. In some embodiments, the method comprises introducing a detection probe as provided in Table 8 and administering an active agent from Table 8 which corresponds to the introduced detection probe.

TABLE 8

Table providing markers and corresponding active agents.

| Marker | Stain | Active Agent |
|---|---|---|
| EGFR | Membrane/cytoplasimic | Erlotini, Afatinib, Gefitinib |
| ALK | Cytoplasmic | Crizotinib, Ceritinib |
| HER2 | Membrane | Herceptin, Perjeta, Kadcyla, Lapatinib) |
| HPV | Nuclear | |
| OX40 | Membrane | Agonist In Development |
| CTLA-4 | Membrane/cytoplasimic | Tremelimumab |

Protocols

Tables 9 and 10 outline two protocols for multiplex detection. The skilled artisan will appreciate that the protocols outlined in Tables 9 and 10 are non-limiting and may be adapted such that different detection probes and detection reagents may be substituted.

TABLE 9

Procedure: U 5-Plx DAB_Gray_Blu_Pur_Gree.37 (v1.00.0270)

| Protocol No | Protocol Name | Creation Date |
|---|---|---|
| 1735 | PD-L1 CC1.56@100.12.ampCD8-32TStr@42-32 | Jul. 6, 2015 |
| 1 | Baking [Selected] | |
| 2 | Warmup Slide to [60 Deg C.], and incubate for [4 Minutes] (Baking) | |
| 3 | Paraffin [Selected] | |

TABLE 9-continued

Procedure: U 5-Plx DAB_Gray_Blu_Pur_Gree.37 (v1.00.0270)

| Protocol No | Protocol Name | Creation Date |
|---|---|---|
| 4 | Alternate Deparaffinization [Selected] | |
| 5 | Cell Conditioning [Selected] | |
| 6 | Cell Conditioning Option [Selected] | |
| 7 | CC1 [Selected] | |
| 8 | Warmup Slide to [100 Deg C.], and Incubate for [4 Minutes] (Cell Conditioner #1) | |
| 9 | CC1 8 Min [Selected] | |
| 10 | CC1 16 Min [Selected] | |
| 11 | CC1 24 Min [Selected] | |
| 12 | CC1 32 Min [Selected] | |
| 13 | CC1 40 Min [Selected] | |
| 14 | CC1 48 Min [Selected] | |
| 15 | CC1 56 Min [Selected] | |
| 16 | DAB [Selected] | |
| 17 | Inhibitor [Selected] | |
| 18 | Antibody [Selected] | |
| 19 | Apply One Drop of [PREP KIT 42] (Antibody), and Incubate for [0 Hr 12 Min] PDL1 (SP 142) | |
| 20 | OptiView Amplification [Selected] | |
| 21 | Apply One Drop of OV AMP H2O2 and One Drop of OV AMPLIFIER, Apply Coverslip, Incubate for [4 Minutes] | |
| 22 | Apply One Drop of OV AMP MULTIMER, Apply Coverslip, and Incubate for [4 Minutes] | |
| 23 | Stringency Wash #2 [Selected] | |
| 24 | Silver Wash in option Bottle Warmup Slide to [42 Deg C.] (Stringency Wash #2) | |
| 25 | Incubate for [32 Minutes] (Stringency Wash #2) | |
| 26 | DISCOVERY Purple [Selected] | |
| 27 | 3rd Antibody [Selected] | |
| 28 | Apply One Drop of [PREP KIT 8] (2nd Antibody), and Incubate for [0 Hr 32 Min] CD 8-spring Conc. 1:50 in 219 | |
| 29 | Research Fork #11 [Selected] Counterstain 5 Disco purple | |
| 30 | Apply One Drop of COUNTERSTAIN 6, and Incubate for [0 Hr 32 Min] Disco purple H2O2 | |
| 31 | Counterstain [Selected] | |
| 32 | Use EZPrep for Counterstain [Selected] | |
| 33 | Apply One Drop of [HEMATOXYLIN II] (Counterstain), Apply Coverslip, and Incubate for [4 Minutes] | |
| 34 | Post Counterstain [Selected] | |
| 35 | Apply One Drop of [BLUING REAGENT] (Post Counterstain), Apply Coverslip, and Incubate for [4 Minutes] | |
| 1 | Enable Mixers | |
| 2 | [This procedure uses the OPTION #4 dispenser for PSS Diluent if Antibody Block# is selected.] | |
| 3 | [This procedure uses the OPTION #6 dispenser for the BLOXALL if Option is selected.] | |
| 4 | Warmup Slide to [60 Deg C.], and Incubate for [4 Minutes] (Baking) | |
| 5 | [LCS Depar] | |
| 6 | Enable Mixers | |
| 7 | Warmup Slide to 58 Deg C., and Incubate for 4 Minutes | |
| 8 | Apply CC Coverslip Long | |
| 9 | Apply CC Coverslip Long | |
| 10 | Apply Depar Volume Adjust | |
| 11 | Warmup Slide to 68 Deg C., and Incubate for 8 Minutes | |
| 12 | Warmup Slide to 36 Deg C. | |
| 13 | [Cell Conditioning Option is TM CC. If not selected will performregular CC.] | |
| 14 | Rinse Slide With EZ Prep | |
| 15 | Apply Long Cell Conditioner #1 | |
| 16 | Apply CC Coverslip Long | |
| 17 | Warmup Slide to [100 Deg C.], and Incubate for [4 Minutes] (Cell Conditioner #1) | |
| 18 | [Nominal temperature selection: 93 degrees] | |
| 19 | Apply Cell Conditioner #1 | |
| 20 | Apply CC Medium Coverslip No BB | |
| 21 | Incubate for 4 Minutes | |
| 22 | Incubate for 8 Minutes | |
| 23 | Apply Cell Conditioner #1 | |
| 24 | Apply CC Medium Coverslip No BB | |
| 25 | Incubate for 8 Minutes | |
| 26 | Incubate for 8 Minutes | |

TABLE 9-continued

Procedure: U 5-Plx DAB_Gray_Blu_Pur_Gree.37 (v1.00.0270)

| Protocol No | Protocol Name | Creation Date |
|---|---|---|
| 27 | Apply Cell Conditioner #1 | |
| 28 | Apply CC Medium Coverslip No BB | |
| 29 | Incubate for 8 Minutes | |
| 30 | Incubate for 8 Minutes | |
| 31 | Apply Cell Conditioner #1 | |
| 32 | Apply CC Medium Coverslip No BB | |
| 33 | Incubate for 8 Minutes | |
| 34 | Apply Cell Conditioner #1 | |
| 35 | Apply CC Medium Coverslip No BB | |
| 36 | Warmup Slide to 37 Deg C. | |
| 37 | Apply Cell Conditioner #1 | |
| 38 | Apply CC Medium Coverslip No BB | |
| 39 | Warmup Slide to 36 Deg C. | |
| 40 | Warmup Slide to 36 Deg C. | |
| 41 | [1st detection is oView DAB] | |
| 42 | [Inhibitor in Reaction Buffer for 8 minutes] | |
| 43 | Rinse Slide With Reaction Buffer | |
| 44 | Adjust slide Volume With Reaction Buffer | |
| 45 | Apply One Drop of OV PEROX IHBTR, Apply Coverslip, and Incubate for 8 Minutes | |
| 46 | Rinse Slide With Reaction Buffer | |
| 47 | Adjust Slide Volume With Reaction Buffer | |
| 48 | Apply Coverslip | |
| 49 | Warmup Slide to 36 Deg C. | |
| 50 | Rinse Slide With Reaction Buffer | |
| 51 | Adjust Slide Volume With Reaction Buffer | |
| 52 | Apply Coverslip | |
| 53 | Rinse Slide With Reaction Buffer | |
| 54 | Adjust Slide Volume With Reaction Buffer | |
| 55 | Apply Coverslip | |
| 56 | [Titration will only happen if selected] | |
| 57 | Apply One Drop of [PREP KIT 42] (Antibody), and Incubate for [0 Hr 12 Min] | |
| 58 | Rinse Slide With Reaction Buffer | |
| 59 | Apply 230 ul + VA Reaction Buffer | |
| 60 | Apply Coverslip | |
| 61 | Rinse Slide With Reaction Buffer | |
| 62 | Adjust Slide Volume With Reaction Buffer | |
| 63 | Apply One drop of OV HQ UNIV LINKR, Apply Coverslip, and Incubate for 12 Minutes | |
| 64 | Rinse Slide With Reaction Buffer | |
| 65 | Apply 230 ul + VA Reaction Buffer | |
| 66 | Apply Coverslip | |
| 67 | Rinse Slide With Reaction Buffer | |
| 68 | Apply 230 ul + VA Reaction Buffer | |
| 69 | Apply Coverslip | |
| 70 | Rinse Slide With Reaction Buffer | |
| 71 | Adjust Slide Volume With Reaction Buffer | |
| 72 | Apply One drop of OV HRP MULTIMER, Apply Coverslip, and Incubate for 12 Minutes | |
| 73 | Rinse Slide With Reaction Buffer | |
| 74 | Apply 230 ul + VA Reaction Buffer | |
| 75 | Apply Coverslip | |
| 76 | Rinse Slide With Reaction Buffer | |
| 77 | Apply 230 ul + VA Reaction Buffer | |
| 78 | Apply Coverslip | |
| 79 | Rinse Slide With Reaction Buffer | |
| 80 | Adjust Slide Volume With Reaction Buffer | |
| 81 | [OptiView Amplifier and OptiView Amplification H2O2 incubation time] | |
| 82 | Apply One drop of OV AMP H2O2 and One Drop of OV AMPLIFIER, Apply Coverslip, Incubate for [4 Minutes] | |
| 83 | Rinse Slide With Reaction Buffer | |
| 84 | Apply 230 ul + VA Reaction Buffer | |
| 85 | Apply Coverslip | |
| 86 | Rinse Slide With Reaction Buffer | |
| 87 | Apply 230 ul + VA Reaction Buffer | |
| 88 | Apply Coverslip | |
| 89 | Rinse Slide With Reaction Buffer | |
| 90 | Adjust Slide Volume With Reaction Buffer | |
| 91 | [OptiView Amplification Multimer incubation time] | |
| 92 | Apply One drop of OV AMP MULTIMER, Apply Coverslip, and Incubate for [4 Minutes] | |
| 93 | Rinse Slide With Reaction Buffer | |
| 94 | Apply 230 ul + VA Reaction Buffer | |
| 95 | Apply Coverslip | |
| 96 | Rinse Slide With Reaction Buffer | |
| 97 | Apply 230 ul + VA Reaction Buffer | |
| 98 | Apply Coverslip | |
| 99 | Rinse Slide With Reaction Buffer | |
| 100 | Adjust Slide Volume With Reaction Buffer | |
| 101 | Apply One Drop of OV H2O2 and One Drop of OV DAB, Apply Coverslip, Incubate for 8 Minutes | |
| 102 | Rinse Slide With Reaction Buffer | |
| 103 | Adjust Slide Volume With Reaction Buffer | |
| 104 | Apply One Drop of OV COPPER, Apply Coverslip, and Incubate for 4 Minutes | |
| 105 | Rinse Slide With Reaction Buffer | |
| 106 | Adjust Slide Volume With Reaction Buffer | |
| 107 | Apply Coverslip | |
| 108 | [SWI buffer at 36 degrees for 4minutes] | |
| 109 | [If step should read "Low pH Enzyme Inactivation and Antibody Elution") | |
| 110 | Warmup Slide to [42 Deg C.) (Stringency Wash #2) | |
| 111 | Rinse Slide With Option | |
| 112 | Apply 300 ul of Option | |
| 113 | Apply Coverslip | |
| 114 | Apply One Drop of OPTION 6, and Incubate for 4 Minutes | |
| 115 | Incubate for [32 Minutes] (Stringency Wash #2) | |
| 116 | Rinse Slide With Reaction Buffer | |
| 117 | Adjust Slide Volume With Reaction Buffer | |
| 118 | Apply Coverslip | |
| 119 | Warmup Slide to 36 Deg C. | |
| 120 | Warmup Slide to 36 Deg C. | |
| 121 | [Discovery Purple is TAMRA] | |
| 122 | [3rd detection is ultraView Red] | |
| 123 | Rinse Slide With Reaction Buffer | |
| 124 | Adjust Slide Volume With Reaction Buffer | |
| 125 | Apply Coverslip | |
| 126 | Apply One Drop of [PREP KIT 8] (2nd Antibody), and Incubate for [0 Hr 32 Min] | |
| 127 | Rinse Slide With Reaction Buffer | |
| 128 | Rinse Slide With Reaction Buffer | |
| 129 | Adjust Slide Volume With Reaction Buffer | |
| 130 | Apply Coverslip | |
| 131 | Rinse Slide With Reaction Buffer | |
| 132 | Adjust Slide Volume With Reaction Buffer | |
| 133 | Rinse Slide With Reaction Buffer | |
| 134 | Adjust Slide Volume With Reaction Buffer | |
| 135 | Apply One Drop of OV HQ UNIV LINKR, Apply Coverslip, and Incubate for 12 Minutes | |
| 136 | Rinse Slide With Reaction Buffer | |
| 137 | Apply 230 ul + VA Reaction Buffer | |
| 138 | Apply Coverslip | |
| 139 | Rinse Slide With Reaction Buffer | |
| 140 | Apply 230 ul + VA Reaction Buffer | |
| 141 | Apply Coverslip | |
| 142 | Rinse Slide With Reaction Buffer | |
| 143 | Adjust Slide Volume With Reaction Buffer | |
| 144 | Apply One Drop of OV HRP MULTIMER, Apply Coverslip, and Incubate for 12 Minutes | |
| 145 | Rinse Slide With Reaction Buffer | |
| 146 | Apply 230 ul + VA Reaction Buffer | |
| 147 | Apply Coverslip | |
| 148 | Rinse Slide With Reaction Buffer | |
| 149 | Apply 230 ul + VA Reaction Buffer | |
| 150 | Apply Coverslip | |
| 151 | Rinse Slide With Reaction Buffer | |
| 152 | Adjust Slide Volume Wth Reaction Buffer | |
| 153 | Apply Coverslip | |
| 154 | [Discovery Purple is in COUNTERSTAIN#5 and H2O2 is in COUNTERSTAIN#6] | |
| 155 | [RF11: Discovery Purple chromogenapplies two drops of chromogen and Incubates for 4 minutes.] | |
| 156 | [Followed by 1 drop of H2O2 and selectable Incubation.] | |
| 157 | Apply Two Drops of COUNTERSTAIN 5, Apply Coverslip, and Incubate for 4 Minutes | |
| 158 | Apply One Drop of COUNTERSTAIN 6, and Incubate for [0 Hr 32 Min] | |
| 159 | Rinse Slide With Reaction Buffer | |

TABLE 9-continued

Procedure: U 5-Plx DAB_Gray_Blu_Pur_Gree.37 (v1.00.0270)

| Protocol No | Protocol Name | Creation Date |
|---|---|---|
| 160 | Adjust Slide Volume Wth Reaction Buffer | |
| 161 | Apply Coverslip | |
| 162 | Rinse Slide With EZ Prep | |
| 163 | Adjust Slide Volume With EZ Prep | |
| 164 | Apply One Drop of [HEMATOXYLIN II] (Counterstain), Apply Coverslip, and Incubate for [4 Minutes] | |
| 165 | Rinse Slide With EZ Prep | |
| 166 | Adjust Slide Volume Wth EZ Prep | |
| 167 | Apply Coverslip | |
| 168 | Rinse Slide With Reaction Buffer | |
| 169 | Adjust Slide Volume With Reaction Buffer | |
| 170 | Apply One Drop of [BLUING REAGENT] (Post Counterstain), Apply Coverslip, and Incubate for [4 Minutes] | |
| 171 | Rinse Slide With Reaction Buffer | |
| 172 | Apply Coverslip | |
| 173 | Disable Slide Heater | |

TABLE 10

Procedure: U 4-Plx_TAM_Rho_CY5_Dabsyl 46 (v1.00.0280)

| Protocol No | Protocol Name | Creation Date |
|---|---|---|
| 1587 | CC32PDL32T40LCA32Cy512St32@42 + PSS | Jul. 6, 2015 |

1. Baking [Selected]
2. Warmup Slide to [60 Deg C.], and Incubate for [4 Minutes] (Baking)
3. Research Fork #1 [Selected]
4. Deparaffinization [Selected]
5. Cell Conditioning [Selected]
6. Ultra CC1 [Selected]
7. Warmup Slide to [93 Deg C.], and Incubate for 4 Minutes (Cell Conditioner #1)
8. CC1 8 Min [Selected]
9. CC1 16 Min [Selected]
10. CC1 24 Min [Selected]
11. CC1 32 Min [Selected]
12. Warmup Slide to [36 Deg C.] (Stringency Wash #1) option bottle w/silver wash
13. Incubate for [32 Minutes] (Stringency Wash #1)
14. DISCOVERY Purple [Selected]
15. Inhibitor [Selected] Disco 760-4840
16. Antibody [Selected]
17. Apply One Drop of [PREP KIT 63] (Antibody), and Incubate for [0 Hr 32 Min] PDL1 (SP263)
18. Rabbit Antibody [Selected]
19. Research Fork #11 [Selected]
20. Apply One Drop of COUNTERSTAIN 6, and Incubate for [0 Hr 40 Min]
21. Stringency Wash #3 [Selected]
22. Warmup Slide to [42 Deg C.] (Stringency Wash #3)
23. Incubate for [32 Minutes] (Stringency Wash #3)
24. Blue [Selected]
25. 3rd Antibody [Selected]
26. Antibody Block 3 [Selected] PSS w/casein (219)
27. Apply One Drop of [OPTION 2] (Option), Apply Coverslip, and Incubate for 4 Minutes Antibody Dil 219
28. Apply One Drop of [ANTI-LCA] (DS Primary Antibody), and Incubate for [0 Hr 32 Min]
29. Research Fork #21 [Selected]
30. Apply One Drop of Anti-Mouse NP, Apply Coverslip, and Incubate for [8 Minutes] Disco 760-4816
31. Apply One Drop of Anti-NP AP, Apply Coverslip, and Incubate for [8 Minutes] Disco 760-4827
32. Apply One Drop of COUNTERSTAIN 9, and Incubate for [0 Hr 12 Min] C4-5 (Qmp) + Counterstain 2-pH Adjust
33. Counterstain [Selected]
34. Use EZPrep for Counterstain [Selected]
35. Apply One Drop of [HEMATOXYLIN II] (Counterstain), Apply Coverslip, and Incubate for [4 Minutes]

TABLE 10-continued

Procedure: U 4-Plx_TAM_Rho_CY5_Dabsyl 46 (v1.00.0280)

36. Post Counterstain [Selected]
37. Apply One Drop of [BLUING REAGENT] (Post Counterstain), Apply Coverslip, and Incubate for [4 Minutes]

| Step No | Procedure Step |
|---|---|

1. Enable Mixers
2. [THIS PROCEDURE USES TYRAMIDE MEDIATED BRIGHTFIELD FLUOROPHORES FOR 1ST AND 2ND]
3. [THIS PROCEDURE USES QUINONE METHIDE MEDIATED BRIGHTFIELD FLUOROPHORES FOR 3RD AND 4TH MARKERS]
4. [This procedure uses the OPTION #4 dispenser for PSS Diluent if Antibody Block# is selected.]
5. [This procedure uses the OPTION #8 dispenser for the BLOXALL if Option is selected.]
6. Warmup Slide to [60 Deg C.], and Incubate for [4 Minutes] (Baking)
7. [Research Fork#1 is the regular TM LCS Depar, Pretreatment and Cell Conditioning]
8. Warmup Slide to 58 Deg C., and Incubate for 4 Minutes
9. Apply CC Coverslip Long
10. Apply CC Coverslip Long
11. Apply EZPrep Volume Adjust
12. Warmup Slide to 68 Deg C., and Incubate for 4 Minutes
13. Rinse Slide With EZ Prep
14. Apply EZPrep Volume Adjust
15. Apply Coverslip
16. Rinse Slide With EZ Prep
17. Apply EZPrep Volume Adjust
18. Apply Coverslip
19. Rinse Slide With EZ Prep
20. Apply Depar Volume Adjust
21. Apply Coverslip
22. Rinse Slide With EZ Prep
23. Apply Long Cell Conditioner #1
24. Apply CC Coverslip Long
25. [93-95° C is the standard temperature]
26. Warmup Slide to [93 Deg C.], and Incubate for 4 Minutes (Cell Conditioner #1)
27. Incubate for 4 Minutes
28. Apply Cell Conditioner #1
29. Apply CC Medium Coverslip No BB
30. Incubate for 8 Minutes
31. Incubate for 8 Minutes
32. Apply Cell Conditioner #1
33. Apply CC Medium Coverslip No BB
34. Incubate for 8 Minutes
35. Apply Cell Conditioner #1
36. Apply CC Medium Coverslip No BB
37. Disable Slide Heater
38. Apply Cell Conditioner #1
39. Apply CC Medium Coverslip No BB
40. [save for CC2]
41. Warmup Slide to 36 Deg C.
42. Rinse Slide With Reaction Buffer
43. Adjust Slide Volume Wth Reaction Buffer
44. Apply Coverslip
45. [SWII buffer at 36 degrees for 4minutes]
46. [If step should read "Low pH Enzyme Inactivation and Antibody Elution"]
47. Warmup Slide to [36 Deg C.] (Stringency Wash #1)
48. Rinse Slide With Option
49. Apply 300 ul of Option
50. Apply Coverslip
51. Apply One Drop of OPTION 8, and Incubate for 4 Minutes Bloyall (vector) Sp6000
52. Incubate for [32 Minutes] (Stringency Wash #1)
53. Rinse Slide With Reaction Buffer
54. Adjust Slide Volume With Reaction Buffer
55. Apply Coverslip
56. [Discovery Purple is TAMRA]
57. [Inhibitor in Reaction Buffer for 8 minutes]
58. Rinse Slide With Reaction Buffer
59. Adjust Slide Volume With Reaction Buffer
60. Apply One Drop of DISC Inhibitor, Apply Coverslip, and Incubate for 8 Minutes 4840
61. Rinse Slide With Reaction Buffer TABLE 10-continued Procedure: U 4-Plx_TAM_Rho_CY5_Dabsyl 46 (v1.00.0280)

| | |
|---|---|
| 62 | Adjust Slide Volume With Reaction Buffer |
| 63 | Apply Coverslip |
| 64 | Rinse Slide With Reaction Buffer |
| 65 | Adjust Slide Volume With Reaction Buffer |
| 66 | [Antibody block 1 drop of OPTIONdipenser to primary Ab and co-incubates.] |
| 67 | Apply Coverslip |
| 68 | Apply One Drop of [PREP KIT 63] (Antibody), and Incubate for [0 Hr 32 Min] |
| 69 | Rinse Slide With Reaction Buffer |
| 70 | Apply 230 ul + VA Reaction Buffer |
| 71 | Apply Coverslip |
| 72 | Rinse Slide With Reaction Buffer |
| 73 | Adjust Slide Volume With Reaction Buffer |
| 74 | Apply One Drop of Anti-Rabbit HQ, Apply Coverslip, and Incubate for 0 Hr 16 Min |
| 75 | Rinse Slide Wth Reaction Buffer |
| 76 | Apply 230 ul + VA Reaction Buffer |
| 77 | Apply Coverslip |
| 78 | Rinse Slide With Reaction Buffer |
| 79 | Apply 230 ul + VA Reaction Buffer |
| 80 | Apply One Drop of Anti-HQ HRP, Apply Coverslip, and Incubate for 12 Minutes |
| 81 | Rinse Slide With Reaction Buffer |
| 82 | Apply 230 ul + VA Reaction Buffer |
| 86 | Rinse Slide With Reaction Buffer |
| 84 | Apply Coverslip |
| 85 | Rinse Slide With Reaction Buffer |
| 86 | Apply 230 ul + VA Reaction Buffer |
| 87 | Apply Coverslip |
| 88 | Rinse Slide With Reaction Buffer |
| 89 | Adjust Slide Volume With Reaction Buffer |
| 90 | Apply Coverslip |
| 91 | [Discovery Purple is in COUNTERSTAIN#5 and H2O2 is in COUNTERSTAIN#6] |
| 92 | [RF11: Discovery Purple chromogenapplies two drops of chromogen and incubates for 4 minutes.] |
| 93 | [Followed by 1 drop of H2O2 and selectable incubation.] |
| 94 | Apply Two Drops of COUNTERSTAIN 5, Apply Coverslip, and Incubate for 4 Minutes |
| 95 | Apply One Drop of COUNTERSTAIN 6, and Incubate for [0 Hr 40 Min] |
| 96 | Rinse Slide With Reaction Buffer |
| 97 | Adjust Slide Volume With Reaction Buffer |
| 98 | Apply Coverslip |
| 99 | [SWII buffer at 36 degrees for 4 minutes] |
| 100 | [If step should read "Low pH Enzyme Inactivation and Antibody Elution"] |
| 101 | Warmup Slide to [42 Deg C.] (Stringency Wash #3) |
| 102 | Rinse Slide With Option |
| 103 | Apply 300 ul of Option |
| 104 | Apply Coverslip |
| 105 | Apply One Drop of OPTION 8, and Incubate for 4 Minutes |
| 106 | Incubate for [32 Minutes] (Stringency Wash #3) |
| 107 | Rinse Slide With Reaction Buffer |
| 108 | Adjust Slide Volume With Reaction Buffer |
| 109 | Apply Coverslip |
| 110 | (Blue is CY5 Quinone Methide) |
| 111 | Rinse Slide With Reaction Buffer |
| 112 | Adjust Slide Volume With Reaction Buffer |
| 113 | Apply Coverslip |
| 114 | Rinse Slide With Reaction Buffer |
| 115 | Adjust Slide Volume With Reaction Buffer |
| 116 | [Antibody block 1 drop of OPTIONdipenser to primary Ab and co-incubates.] |
| 117 | Apply One Drop of [OPTION 2] (Option), Apply Coverslip, and Incubate for 4 Minutes |
| 118 | [Antibody block 1 drop of OPTIONdipenser to primary Ab and co-incubates.] |
| 119 | Apply Coverslip |
| 120 | Apply One Drop of [ANTI-LCA] (DS Primary Antibody), and Incubate for [0 Hr 32 Min] |
| 121 | Rinse Slide With Reaction Buffer |
| 122 | Apply 230 ul + VA Reaction Buffer |
| 123 | Apply Coverslip |
| 124 | Rinse Slide With Reaction Buffer |
| 125 | Apply 230 ul + VA Reaction Buffer |
| 126 | Apply Coverslip |
| 127 | Rinse Slide With Reaction Buffer |
| 128 | Adjust Slide Volume With Reaction Buffer |
| 129 | [Anti-Mouse Linker-NP] |
| 130 | Apply One Drop of Anti-Mouse NP, Apply Coverslip, and Incubate for [8 Minutes] |
| 131 | Rinse Slide With Reaction Buffer |
| 132 | Apply 230 ul + VA Reaction Buffer |
| 133 | Apply Coverslip |
| 134 | Rinse Slide With Reaction Buffer |
| 135 | Adjust Slide Volume With Reaction Buffer |
| 136 | Apply One Drop of Anti-NP AP, Apply Coverslip, and Incubate for [8 Minutes] |
| 137 | Rinse Slide With Reaction Buffer |
| 138 | Apply 230 ul + VA Reaction Buffer |
| 139 | Apply Coverslip |
| 140 | Rinse Slide With SSC |
| 141 | Adjust Slide Volume With SSC |
| 142 | Apply Coverslip |
| 143 | Rinse Slide With SSC |
| 144 | Adjust Slide Volume With SSC |
| 145 | [pH adjust in COUNTERSTAIN#2 and CY5 Quinone Methide in COUNTERSTAIN#9.] |
| 146 | Apply Two Drops of COUNTERSTAIN 2, Apply Coverslip, and Incubate for 4 Minutes |
| 147 | Apply One Drop of COUNTERSTAIN 9, and Incubate for [0 Hr 12 Min] |
| 148 | Rinse Slide With Reaction Buffer |
| 149 | Adjust Slide Volume With Reaction Buffer |
| 150 | Apply Coverslip |
| 151 | Rinse Slide With EZ Prep |
| 152 | Adjust Slide Volume With EZ Prep |
| 153 | Apply One Drop of [HEMATOXYLIN II] (Counterstain), Apply Coverslip, and Incubate for (4 Minutes) |
| 154 | Rinse Slide With EZ Prep |
| 155 | Adjust Slide Volume With EZ Prep |
| 156 | Apply Coverslip |
| 157 | Rinse Slide With Reaction Buffer |
| 158 | Adjust Slide Volume With Reaction Buffer |
| 159 | Apply One Drop of [BLUING REAGENT] (Post Counterstain), Apply Coverslip, and Incubate for [4 Minutes] |
| 160 | Rinse Slide With Reaction Buffer |
| 161 | Apply Coverslip |
| 162 | Disable Slide Heater |

Additional Targets and Detection Probes

In some embodiments, the multiplex assays, kits, and methods disclosed herein comprise detecting other targets in addition to PD-L1 and immune cell markers. Therefore, in some embodiments, the assays, kits, and methods herein comprise additional detection probes (e.g. nucleic acid probes or primary antibodies or any combination thereof) to detect additional targets, such as those additional targets described below. In some embodiments, the other targets are tumor markers other than PD-L1. In some embodiments, the assays, kits, and methods may include a detection probe specific for one or more of EGFR, HER2, HPV, ALK, BRAF, OX-40, PD-1 IDO-1, FoxP3, CD163, and CTLA-4. The skilled artisan will recognize that any number of additional detection probes may be included in any multiplex assay, kit or method. The skilled artisan will also be able to selected appropriate detection reagents to best detect the additional detection probes, such as detection reagents that provide good contrast (as defined herein) or utilizing any combination of chromogens, fluorophores, etc.

Throughout this disclosure when reference is made to a target protein it is understood that the nucleic acid sequences associated with that protein can also be used as a target. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

In some embodiments, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemia, lymphomas, breast cancer, colon cancer, neurological cancers and the like. Therefore, in some embodiments, at least a portion of the target molecule is produced by a nucleic acid sequence (e.g., genomic target nucleic acid sequence) amplified or deleted in at least a subset of ceils in a sample.

Oncogenes are known to be responsible for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When detection probes corresponding to these target nucleic acid sequences (e.g., genomic target nucleic acid sequences) are used in an in situ hybridization procedure, normal cells, which lack a t(18q11.2) in the SYT gene region, exhibit two fusion (generated by the two labels in close proximity) signals, reflecting the two intact copies of SYT. Abnormal cells with a t(18q11.2) exhibit a single fusion signal.

In other embodiments, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC-000007, nucleotides 55054219-55242525), the C-MYC gene (8q24.21; e.g., GENBANK™ Accession No. NC-000008, nucleotides 128817498-128822856), D5S271 (5p15.2), lipoprotein lipase (LPL) gene (8p22; e.g., GENBANK™ Accession No. NC-000008, nucleotides 19841058-19869049), RB1 (13q14; e.g., GENBANK™ Accession No. NC-000013, nucleotides 47775912-47954023), p53 (17p13.1; e.g., GENBANK™ Accession No. NC-000017, complement, nucleotides 7512464-7531642)), N-MYC (2p24; e.g., GENBANK™ Accession No. NC-000002, complement, nucleotides 151835231-151854620), CHOP (12q13; e.g., GENBANK™ Accession No. NC-000012, complement, nucleotides 56196638-56200567), FUS (16p11.2; e.g., GENBANK™ Accession No. NC-000016, nucleotides 31098954-31110601), FKHR (13p14; e.g., GENBANK™ Accession No. NC-000013, complement, nucleotides 40027817-40138734), as well as, for example: ALK (2p23; e.g., GENBANK™ Accession No. NC-000002, complement, nucleotides 29269144-29997936), Ig heavy chain, CCNDI (11q13; e.g., GENBANK™ Accession No. NC-000011, nucleotides 69165054.69178423), BCL2 (18q21.3; e.g., GENBANK™ Accession No. NC-000018, complement, nucleotides 58941559-59137593), BCL6 (3q27; e.g., GENBANK™ Accession No. NC-000003, complement, nucleotides 138921859-188946169), MALF1, AP1 (1p32-p31; e.g., GENBANK™ Accession No. NC-000001, complement, nucleotides 59019051-59022373), TOP2A (17q21-q22; e.g., GENBANK™ Accession No. NC-000017, complement, nucleotides 35798321-35827695), TMPRSS (21q22.3; e.g., GENBANK™ Accession No. NC-000021, complement, nucleotides 41758351-41801948), ERG (21q22.3; e.g., GENBANK™ Accession No. NC-000021, complement, nucleotides 38675671-38955488); ETV1 (7p21.3; e.g., GENBANK™ Accession No. NC-000007, complement, nucleotides 13897379-13995289), EWS (22q12.2; e.g., GENBANK™ Accession No. NC-000022, nucleotides 27994271-28026505); FL11 (11q24.1-q24.3; e.g., GENBANK™ Accession No. NC-000011, nucleotides 128069199-128187521), PAX3 (2q35-q37; e.g., GENBANK™ Accession No. NC-000002, complement, nucleotides 222772851-222871944), PAX7 (1p36.2-p36.12; e.g., GENBANK™ Accession No. NC-000001, nucleotides 18830087-18935219), PTEN (10q23.3; e.g., GENBANK™ Accession No. NC-000010, nucleotides 89613175-89716382), AKT2 (19q13.1-q13.2; e.g., GENBANK™ Accession No. NC-000019, complement, nucleotides 45431556-45483036), MYCL1 (1p34.2; e.g., GENBANK™ Accession No. NC-000001, complement, nucleotides 40133685-40140274), REL (2p13-p12; e.g., GENBANK™ Accession No. NC-000002, nucleotides 60962256-61003682) and CSF1R (5q33-q35; e.g., GENBANK™ Accession No. NC-000005, complement, nucleotides 149413051-149473128).

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum, Entamoeba histolytica,* and *Giardia lamblia,* as well as *Toxoplasma, Eimeria, Theileria,* and *Babesia* species).

In some examples, the target protein is produced from a nucleic acid sequence (e.g., genomic target nucleic acid sequence) from a viral genome. Exemplary viruses and corresponding, genomic sequences (GENBANK™ RefSeq Accession No. in parentheses) include human adenovirus A (NC-001460), human adenovirus B (NC-004001), human adenovirus C (NC-001405), human adenovirus D (NC-002067), human adenovirus E (NC-003266), human adenovirus F (NC-001454), human astrovirus (NC-001943), human BK polyomavirus (V01109; GI:60851) human bocavirus (NC-007455), human coronavirus 229E (NC-002645), human coronavirus HKU1 (NC-006577), human coronavirus NL63 (NC-005831), human coronavirus OC43 (NC-005147), human enterovirus A (NC-001612), human enterovirus B (NC-001472), human enterovirus C (NC-001428), human enterovirus D (NC-001430), human erythrovirus V9 (NC-004295), human foamy virus (NC-001736), human herpesvirus 1 (Herpes simplex virus type 1) (NC-001806), human herpesvirus 2 (Herpes simplex virus type 2) (NC-001798), human herpesvirus 3 (Varicella zoster virus) (NC-001348), human herpesvirus 4 type 1 (Epstein-Barr virus type 1) (NC-007605), human herpesvirus 4 type 2 (Epstein-Barr virus type 2) (NC-009334), human herpes virus 5 strain AD 169 (NC-001347), human herpesvirus 5 strain Merlin Strain (NC-006273), human herpes virus 6A (NC-001664), human herpesvirus 6B (NC-000898), human herpesvirus 7 (NC-001716), human herpesvirus 8 type M (NC-003409), human herpesvirus 8 type P (NC-009333), human immunodeficiency virus 1 (NC-001802), human immunodeficiency virus 2 (NC-001722), human metapneumovirus (NC-004148), human papillomavirus-1 (NC-001356), human papillomavirus-18 (NC-001357), human papillomavirus-2 (NC-001352), human papillomavirus-54 (NC-001676), human papillomavirus-61 (NC-001694), human papillomavirus-cand90 (NC-004104), human papillomavirus RTRX7 (NC-004761), human papillomavirus type 10 (NC-001576), human papillomavirus type 101 (NC-008189), human papillomavirus type 103 (NC-008188), human papillomavirus type 107 (NC-009239), human papillomavirus type 16 (NC-001526), human papillomavirus type 24 (NC-001683), human papillomavirus type 26 (NC-001583), human papillomavirus type 32 (NC-001586), human papillomavirus type 34 (NC-001587), human papillomavirus type 4 (NC-001457), human papillomavirus type 41 (NC-001354), human papillomavirus type 48 (NC-001690), human papillomavirus type 49 (NC-001591), human papillomavirus type 5 (NC-001531), human papillomavirus type 50 (NC-001691), human papillomavirus type 53 (NC-001593), human papillomavirus type 60 (NC-001693), human papillomavirus type 63 (NC-001458), human papillomavirus type 6b (NC-001355), human papillomavirus type 7 (NC-001595), human papillomavirus type 71 (NC-002644), human papillomavirus type 9 (NC-001596), human papillomavirus type 92 (NC-004500), human papillomavirus type 96 (NC-005134), human parainfluenza virus 1 (NC-003461), human parainfluenza virus 2 (NC-003443), human parainfluenza virus 3 (NC-001796), human parechovirus (NC-001897), human parvovirus 4 (NC-007018), human parvovirus B19 (NC-000883), human respiratory syncytial virus (NC-001781), human rhinovirus A (NC-001617), human rhinovirus B (NC-001490), human spumaretrovirus (NC-001795), human T-lymphotropic virus 1 (NC-001436), human T-lymphotropic virus 2 (NC-001488).

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

Additional Specific Embodiments

Although the invention herein has been described with reference to particular embodiments, it is to be understood that these embodiments are merely illustrative of the principles and applications of the present invention. It is therefore understood that numerous modifications may be made to the illustrative embodiments and that other arrangements may be devised without departing from the spirit and scope of the present invention as defined by the appended claims.

---

The invention claimed is:

1. An immunohistochemical method of identifying tumor infiltrating PD-L1 positive immune cells in a PD-L1 positive tumor via brightfield microscopy, said method comprising:
contacting a tissue sample with a first primary antibody specific to PD-L1 protein in a manner to effect binding of the first primary antibody to the tissue sample in proximity to PD-L1 protein expressed by the tissue sample;
depositing a first enzyme in proximity to the first primary antibody bound to the tissue sample;
reacting the first enzyme with a first substrate to effect deposition of a first brightfield microscopy-detectable dye on the tissue sample in proximity to the first primary antibody;
contacting the tissue sample with a second primary antibody specific to at least one immune cell marker protein in a manner to effect binding of the second primary antibody to the tissue sample in proximity to immune cell marker protein expressed by the tissue sample;
depositing a second enzyme in proximity to the second primary antibody bound to the tissue sample and
reacting the second enzyme with a second substrate to effect deposition of a second brightfield microscopy-detectable dye on the tissue sample in proximity to the second primary antibody,
wherein (i) the first brightfield microscopy-detectable dye is 4-(dimethylamino) azobenzene-4'-sulfonamide and the second brightfield microscopy-detectable dye is tetramethylrhodamine, or (ii) the first brightfield microscopy-detectable dye is tetramethylrhodamine and the second brightfield microscopy-detectable dye is 4-(dimethylamino) azobenzene-4'-sulfonamide.

2. The method of claim 1, wherein the tumor infiltrating PD-L1 positive immune cells co-express PD-L1 and the at least one immune cell marker.

3. The method of claim 1, wherein the first primary antibody is SP142 or SP263.

4. The method of claim 1, wherein the immune cell marker is selected from the group consisting of CD8, CD4, CD3, CD15, CD163 and CD45LCA.

5. The method of claim 4, wherein the immune cell marker is CD45LCA or CD8.

6. The method of claim 5, wherein the second primary antibody is anti-CD45LCA antibody.

7. The method of claim 1, wherein the first brightfield microscopy-detectable dye is 4-(dimethylamino) azobenzene-4'-sulfonamide and the second brightfield microscopy-detectable dye is tetramethylrhodamine.

8. The method of claim 1, wherein the first brightfield microscopy-detectable dye is applied to the tissue sample before the second brightfield microscopy-detectable dye.

9. The method of claim 1, wherein the first brightfield microscopy-detectable dye or the second brightfield microscopy-detectable dye is deposited via a signaling conjugate comprising a latent reactive moiety configured to react with the enzyme to form a reactive species.

10. The method of claim 9, wherein the latent reactive moiety is directly conjugated to the first brightfield microscopy-detectable dye or the second brightfield microscopy-detectable dye.

11. The method of claim 10, wherein the latent reactive moiety comprises tyramide or a quinone methide (QM) analog.

12. The method of claim 11, wherein the latent reactive moiety comprises tyramide.

13. An immunohistochemical method of identifying PD-L1 positive immune cells in a tumor tissue section, said method comprising:
contacting a tissue sample with a first primary antibody specific to PD-L1 protein in a manner to effect binding of the first primary antibody to the tissue sample in proximity to PD-L1 protein expressed by the tissue sample;
depositing a first enzyme in proximity to the first primary antibody bound to the tissue sample;
reacting the first enzyme with a first substrate to effect deposition of 4-(dimethylamino) azobenzene-4'-sulfonamide on the tissue sample in proximity to the first primary antibody, wherein the 4-(dimethylamino) azobenzene-4'-sulfonamide is deposited via a signaling conjugate comprising tyramide directly conjugated to 4-(dimethylamino) azobenzene-4'-sulfonamide;
contacting the tissue sample with a second primary antibody specific to at least one immune cell marker protein in a manner to effect binding of the second primary antibody to the tissue sample in proximity to immune cell marker protein expressed by the tissue sample;
depositing a second enzyme in proximity to the second primary antibody bound to the tissue sample; and
reacting the second enzyme with a second substrate to effect deposition of tetramethylrhodamine on the tissue sample in proximity to the second primary antibody, wherein the tetramethylrhodamine is deposited via a signaling conjugate comprising tyramide directly conjugated to the tetramethylrhodamine, and
detecting by brightfield microscopy cells that are co-stained with tetramethylrhodamine and 4-(dimethylamino) azobenzene-4'-sulfonamide in the tissue sample, thereby identifying PD-L1 positive immune cells.

* * * * *

UNITED STATES PATENT AND TRADEMARK OFFICE
CERTIFICATE OF CORRECTION

PATENT NO. : 11,899,016 B2
APPLICATION NO. : 15/985638
DATED : February 13, 2024
INVENTOR(S) : Birch Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 718 days.

Signed and Sealed this
Eighth Day of October, 2024

Katherine Kelly Vidal
*Director of the United States Patent and Trademark Office*